United States Patent
Kirshenbaum et al.

(10) Patent No.: US 9,872,495 B2
(45) Date of Patent: *Jan. 23, 2018

(54) PEPTOID OLIGOMERS, PHARMACEUTICAL COMPOSITIONS AND METHODS OF USING THE SAME

(71) Applicants: Kent Kirshenbaum, New York, NY (US); Sung Bin Shin, New York, NY (US)

(72) Inventors: Kent Kirshenbaum, New York, NY (US); Sung Bin Shin, New York, NY (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/093,880

(22) Filed: Apr. 8, 2016

(65) Prior Publication Data

US 2016/0219880 A1    Aug. 4, 2016

Related U.S. Application Data

(63) Continuation of application No. 14/481,148, filed on Sep. 9, 2014, now Pat. No. 9,315,548, which is a continuation of application No. 12/711,663, filed on Feb. 24, 2010, now Pat. No. 8,828,413.

(60) Provisional application No. 61/155,137, filed on Feb. 24, 2009.

(51) Int. Cl.
| | |
|---|---|
| *A01N 43/713* | (2006.01) |
| *C07K 7/64* | (2006.01) |
| *C07K 7/66* | (2006.01) |
| *C07K 7/06* | (2006.01) |
| *A01N 37/26* | (2006.01) |
| *A01N 43/36* | (2006.01) |
| *A01N 43/90* | (2006.01) |
| *A01N 47/44* | (2006.01) |
| *A61K 38/08* | (2006.01) |
| *A61K 38/12* | (2006.01) |
| *A61K 38/00* | (2006.01) |

(52) U.S. Cl.
CPC .......... *A01N 43/713* (2013.01); *A01N 37/26* (2013.01); *A01N 43/36* (2013.01); *A01N 43/90* (2013.01); *A01N 47/44* (2013.01); *C07K 7/06* (2013.01); *C07K 7/64* (2013.01); *C07K 7/66* (2013.01); *A61K 38/00* (2013.01); *A61K 38/08* (2013.01); *A61K 38/12* (2013.01)

(58) Field of Classification Search
CPC ...... A01N 43/713; A01N 37/26; A01N 43/36; A01N 43/90; A01N 47/44

See application file for complete search history.

(56) References Cited

U.S. PATENT DOCUMENTS

| | | | |
|---|---|---|---|
| 5,877,278 A | 3/1999 | Zuckermann et al. | |
| 7,834,144 B2 | 11/2010 | Peretz et al. | |
| 8,524,663 B2 | 9/2013 | Kirshenbaum et al. | |
| 8,828,413 B2 * | 9/2014 | Kirshenbaum | C07K 7/06 424/405 |
| 9,315,548 B2 * | 4/2016 | Kirshenbaum | A01N 37/26 |
| 2010/0233291 A1 | 9/2010 | Smithynian et al. | |
| 2013/0045941 A1 | 2/2013 | Cozean et al. | |
| 2014/0113862 A1 | 4/2014 | Kirshenbaum et al. | |
| 2014/0274916 A1 | 9/2014 | Kirshenbaum et al. | |
| 2015/0126450 A1 | 5/2015 | Kirshenbaum et al. | |

FOREIGN PATENT DOCUMENTS

| | | |
|---|---|---|
| EP | 1338604 | 8/2003 |
| WO | 199640759 | 12/1996 |
| WO | 2007113531 | 10/2007 |

OTHER PUBLICATIONS

Fowler et al., "Design and synthesis of macrocyclic peptomers as mimics of a quorum sensing from *Staphylococcus aureus*", Organic Letters, 2008, 10:2329-2332.

(Continued)

*Primary Examiner* — Alma Pipic
(74) *Attorney, Agent, or Firm* — Klauber & Jackson LLC

(57) ABSTRACT

Novel peptoid oligomers are disclosed that have a formula represented by the following formula I:

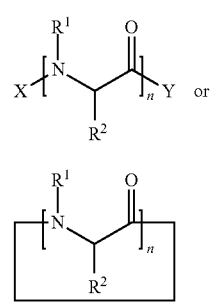

The peptoids demonstrate antimicrobial activity and may be prepared as pharmaceutical compositions and used for the prevention or treatment of a variety of conditions in mammals including humans where microbial invasion is involved. The present cyclic and linear peptoids are particularly valuable as their effect is rapid, broad in spectrum and mostly indifferent to resistance provoked by standard antibiotics.

29 Claims, 6 Drawing Sheets

(56) References Cited

OTHER PUBLICATIONS

Fowler et al., Structure-function relationships in peptoids: recent advances toward deciphering the structural requirements for biological function, Org. Biomol. Chem., Feb. 11, 2009, 7:1508-1524.

Statz et al., "Surface-immobilized antimicrobial peptoides", Biofouling, 2008, 24:439-448.

Chongsiriwatana et al., "Peptoids that mimic the structure, function, and mechanism of helical antimicrobial peptides", Proceedings of the National Academy of Sciences, 2008, 105:2794-2799.

Patch et al., "Helical peptoid mimics of magainin-2 amide", Journal of the American Chemical Society, 2003, 125, 12092-12093.

Holder et al., "Design and pharmacology of peptoids and peptide-peptoid hybrids based on the melanacortin agonists core tetrapeptide sequence", Bioorganic & Medicinal Chemistry Letters, 2003, 13:4505-4509.

Simon et al., "Peptoids: A modular approach to drug discovery", Chemical Proc National Acad Sci, 1992, 89:9367-9371.

Ng et al., "Combinatorial discovery process yields antimicrobial peptoids", Biorganic & Medicinal Chemistry, 1999, 7:1781-1785.

Uttam et al., "First synthesis of n-linked-glycopeptoid as new glycopeptidomimetics", Tetrahedron Letters, 1995, 36:3635-3638.

Miller et al., "Comparison of the proteolytic susceptbilities of homologous L-amino, D-amino acid, and n-substituted glycine and peptoid oligomers", Drug Development Research, 1995, 35:20-32.

Lim et al., Chemical Communication, Published on the web on Jan. 24, 2008, pp. 1064-1066.

Lim et al., Chemical Communication, Published on the web on Jan. 24, 2008, pp. 1064-1066, Electronic Supplementary Information.

Burkoth et al., "Incorporation of unprotected heterocyclic side chains into peptoid oligomers via solid-phase submonomer synthesis", Journal of the American Chemical Society, 2003, 125:8841-8845.

* cited by examiner

PEPTOID OLIGOMERS, PHARMACEUTICAL COMPOSITIONS AND METHODS OF USING THE SAME

CROSS REFERENCE TO RELATED APPLICATION

This application is a Continuation Application of co-pending U.S. application Ser. No. 14/481,148, filed on Sep. 9, 2014, which is a Continuation Application of U.S. application Ser. No. 12/711,663, now U.S. Pat. No. 8,828,413, issued Sep. 9, 2014, which in turn claims priority under 35 USC §119(e) from U.S. Provisional Application Ser. No. 61/155,137, filed Feb. 24, 2009, which application is herein specifically incorporated by reference in its entirety.

FIELD OF THE INVENTION

This invention relates to novel compositions containing active cyclic and/or linear peptoids, and particularly, such cyclic and/or linear peptoids as demonstrate antimicrobial, antifungal, or antiviral activity. The invention also relates to methods for the preparation of the cyclic and/or linear peptoid compositions, and their use in preventing and/or treating conditions resulting from the unwanted presence of microbial, fungal, or viral activity. This invention also relates to use of cyclic and/or linear peptoid compositions in preventing and/or treating conditions resulting from gram positive and gram negative bacterial strains. The invention generally relates to use of cyclic and/or linear peptoid compositions in pharmaceutical, healthcare, medical device, industrial, food, agricultural, and personal care applications.

BACKGROUND OF THE INVENTION

Antimicrobial agents play a crucial role in the treatment of disease. Since the advent of modern antibiotics, it has become apparent that pathogens are capable of developing resistance to antibiotic drug therapy. Increasingly, pathogens that manifest resistance to multiple classes of antibiotics are becoming prevalent, setting the stage for a crisis in global public health. New pharmacological options are urgently needed, preferably including strategies that are likely to remain effective over a sustained course of time.

The incidence of bacterial infections such as methicillin-resistant *Staphylococcus aureus* (MRSA) causes tens of thousands of deaths annually, and leads to more than $2 billion in health care costs. The discovery of new anti-infective agents has been disappointingly slow. One promising strategy is to develop therapeutic compounds that exert their activity on cellular membranes. Microbial species may be incapable of significantly altering the characteristics of their membrane lipid components. This suggests that compounds capable of selectively disrupting microbial membrane function will yield improved drugs that can deter the emergence of antibiotic resistance.

In the field of peptidomimetics research, extensive efforts have been made to recapitulate the structural features present in naturally occurring bioactive peptides (Ripka et al. Curr. Opin. in Chem. Bio. 1998, 2, 441-452; Steer et al. Curr. Med. Chem. 2002, 9, 811-822; Patch et al. Curr. Opin. In Chem. Biol. 2002, 6, 872-877). Many functional peptidomimetics such as magainin mimics (Liu et al. J. Am. Chem. Soc. 2001, 123, 7553-7559; Wieprecht et al. Biochemistry 1996, 35, 10844-10853; Porter et al. J. Am. Chem. Soc. 2005, 127, 11516-11529; Numao et al. Biol. Pharm. Bull. 1997, 20, 800-804; Rennie et al. J. Ind. Microbiol. Biotechnol. 2005, 32, 296-300), integrin mimics (Pasqualini et al. J. Cell Biol. 1995, 130, 1189-1196; Scarborough et al. Curr. Med. Chem. 1999, 6, 971-981) and somatostatin mimics (Gademann et al. J. Med. Chem. 2001, 44, 2460-2468; Gademann et al. Helv. Chim. Acta 2000, 83, 16-33) highlight the significance of structural mimicry for their function. More recently, efforts have been made to enhance the conformational ordering of peptidomimetic oligomers (Fink et al. J. Am. Chem. Soc. 1998, 120, 4334-4344; Phillips et al. J. Am. Chem. Soc. 2002, 124, 58-66; Abell et al. Lett. Pept. Sci. 2001, 8, 267-272; Clark et al. J. Am. Chem. Soc. 1995, 117, 12364-12365; Dimartino et al. Org. Lett. 2005, 7, 2389-2392). Stabilizing or rigidifying polymer conformations may lead to enhanced binding affinities (Sewald et al., Peptides: Chemistry and Biology. Wiley-VCH: Weinheim, Germany: 2002; Wipf. Chem. Rev. 1995, 95, 2115-2134). To this end, several methods have been developed to enhance the conformational ordering of non-natural polymers (Sewald et al., Peptides: Chemistry and Biology. Wiley-VCH: Weinheim, Germany: 2002; Wipf. Chem. Rev. 1995, 95, 2115-2134; Holub et al. Org. Lett. 2007, 9, 3275-3278). These methods include the introduction of both covalent and non-covalent intramolecular interactions. Some examples of covalent constraints include site-specific macrocyclization via Huisgen 1,3-dipolar cycloaddition (Holub et al. Org. Lett. 2007, 9, 3275-3278), head-to-tail macrocyclization (Gademann et al. Angew. Chem., Int. 1999, 38, 1223-1226; Robinson et al. Bioorg. Med. Chem. 2005, 13, 2055-2064; Wels et al. Bioorg. Med. Chem. Lett. 2005, 15, 287-290; Shankaramma et al. Chem. Commun. 2003, 1842-1843; Locardi et al. J. Am. Chem. Soc. 2001, 123, 8189-8196; Chakraborty et al. J. Org. Chem. 2003, 68, 6257-6263; Angell et al. J. Org. Chem. 2005, 70, 9595-9598; Norgren et al. J. Org. Chem. 2006, 71, 6814-6821; Clark et al. J. Am. Chem. Soc. 1998, 120, 651-656; Yuan et al. J. Am. Chem. Soc. 2004, 126, 11120-11121; Nnanabu et al. Org. Lett. 2006, 8, 1259-62; Jiang et al. Org. Lett. 2004, 6, 2985-2988; Mann et al. Org. Lett. 2003, 5, 4567-4570; Wels et al. Org. Lett. 2002, 4, 2173-2176; Bru et al. Tetrahedron Lett. 2005, 46, 7781-7785; Vaz et al. Org. Lett. 2006, 8, 4199-4202; Buttner et al. Chem. Eur. J. 2005, 11, 6145-6158; Royo et al. Tetrahedron Lett. 2002, 43, 2029-2032) and generation of hydrogen bond surrogates via metathesis reactions (Dimartino et al. Org. Lett. 2005, 7, 2389-2392).

Peptoids, for example, are a class of peptidomimetics which comprise N-substituted glycine monomer units (Figliozzi et al, Synthesis of N-substituted glycine peptoid libraries. In Methods Enzymol., Academic Press: 1996; Vol. 267, pp 437-447; Bartlett et al., Proc. Natl. Acad. Sci U.S.A. 1992, 89, 9367-9371). Peptoids are an important class of sequence-specific peptidomimetics shown to generate diverse biological activities (Patch et al. In Pseudo-peptides in Drug Development; Nielson, P. E., Ed.; Wiley-VCH: Weinheim, Germany, 2004; pp 1-35; Miller et al. Drug Dev. Res. 1995, 35, 20-32; Murphy et al. Proc. Natl. Acad. Sci. U.S.A. 1998, 95, 1517-1522; Nguyen et al. Science 1998, 282, 2088-2092; Ng et al. Bioorg. Med. Chem. 1999, 7, 1781-1785; Patch et al. J. Am. Chem. Soc. 2003, 125, 12092-12093; Wender et al. Proc. Natl. Acad. Sci. U.S.A. 2000, 97, 13003-13008; Wu et al. Chem. Biol. 2003, 10, 1057-1063; Chongsiriwatana et al. Proc. Natl. Acad. Sci. U.S.S. 2008, 105, 2794-2799). Oligopeptoids can be designed to display chemical moieties analogous to the bioactive peptide side chains while their abiotic backbones provide protection from proteolytic degradation.

Peptoid sequences comprised of bulky chiral side chains have the capacity to adopt a stable helical secondary structure, although some conformational heterogeneity is evident in solution (Armand et al. *Proc. Natl. Acad. Sci. U.S.A.* 1998, 95, 4309-4314; Kirshenbaum et al. *Proc. Natl. Acad. Sci. U.S.A.* 1998, 95, 4303-4308; Wu et al. *J. Am. Chem. Soc.* 2003, 125, 13525-13530). The crystal structure of a linear peptoid homopentamer composed of bulky chiral side chains exhibits a helical conformation resembling that of a polyproline type I helix (Armand et al. *Proc. Natl. Acad. Sci. U.S.A.* 1998, 95, 4309-4314; Kirshenbaum et al. *Proc. Natl. Acad. Sci. U.S.A.* 1998, 95, 4303-4308; Wu et al. *J. Am. Chem. Soc.* 2003, 125, 13525-13530). Oligopeptoid sequences incorporating repeating units of two bulky chiral side chains and a cationic side chain form facially amphiphilic helical structures. Recent studies describe antimicrobial activities generated from facially amphiphilic helical peptoids (Patch et al. *J. Am. Chem. Soc.* 2003, 125, 12092-12093; Chongsiriwatana et al. *Proc. Natl. Acad. Sci. U.S.S.* 2008, 105, 2794-2799). These peptoid oligomers are reported to be good functional mimics of maganin-2 amide, a peptide antimicrobial agent from *Xenopus* skin (Patch et al. *J. Am. Chem. Soc.* 2003, 125, 12092-12093; Zasloff. *Proc. Natl. Acad. Sci. USA* 1987, 84, 5449-5453).

Antimicrobials can have 'specific mode of action or 'non-specific mode of action. Antimicrobials that undergo 'specific mode of action' inhibit bacterial metabolism and antimicrobials that undergo 'non-specific mode of action' disrupt bacterial membranes (Brogden. *Nat. Tev. Microbiol.* 2005, 3, 238-250). An example of a peptide antimicrobial that undergoes a 'specific mode of action' is penicillin, which inhibits DD-transpeptidase, a bacterial enzyme responsible for cross-linking the peptidoglycan chains that form rigid bacterial cell walls (Waxman et al. *Ann. Rev. Biochem.* 1983, 52, 825-869). Some examples of peptide antimicrobials that undergo 'non-specific mode of action' include maganin 2, protegrin-1, melittin, and alamethicin, all of which disrupt bacterial cell membranes (Waxman et al. *Ann. Rev. Biochem.* 1983, 52, 825-869).

Amphiphilicity is a common structural feature found in peptide antimicrobials, especially the ones that exhibit helical secondary structure (Tossi et al. *Biopolymers* 2000, 55, 4-30). There are three widely accepted mechanisms for helical peptide antimicrobials. These antimicrobials are believed to undergo 'barrel-stave', 'carpet', or 'toroidal-pore' mechanisms (Waxman et al. *Ann. Rev. Biochem.* 1983, 52, 825-869). In all three mechanisms, amphiphilic structure plays a key role in disrupting bacterial membranes.

SUMMARY OF THE INVENTION

In an effort to discover peptoid sequences with enhanced antimicrobial activity, a library of linear and cyclic peptoid oligomers was synthesized. The side chain moieties included in the library contain both direct mimics of peptide side chains and also non-proteinogenic side chains. The inventors demonstrate that the linear and cyclic peptoid oligomers of the present invention are potent and selective antimicrobials. The optimized peptoid sequences are nontoxic to human red blood cells and show potent antimicrobial activities against both gram positive and gram negative bacterial strains, such as *E. coli*, *S. aureus*, and *B. subtilis*.

Accordingly, the present inventors have determined that antibiotic cyclic and linear peptoid oligomers may be prepared that exhibit enhanced stability, due, at least in part, to resistance to enzymatic digestion.

As demonstrated herein, peptoid oligomers of the present invention exhibit antibiotic activity, with minimal host cell toxicity. These findings lead to novel peptoid oligomers that are promising candidates for therapeutic use. It also leads to pharmaceutical compositions comprising the cyclic and/or linear peptoids of the present invention as active ingredients and to their use to treat, prevent or ameliorate a range of conditions in mammals of various genesis or etiology, however, primarily caused by bacteria, viruses, or fungi.

More particularly, the present invention relates to peptoid oligomers having antimicrobial properties, according to formula Ia or Ib:

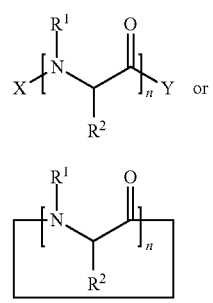

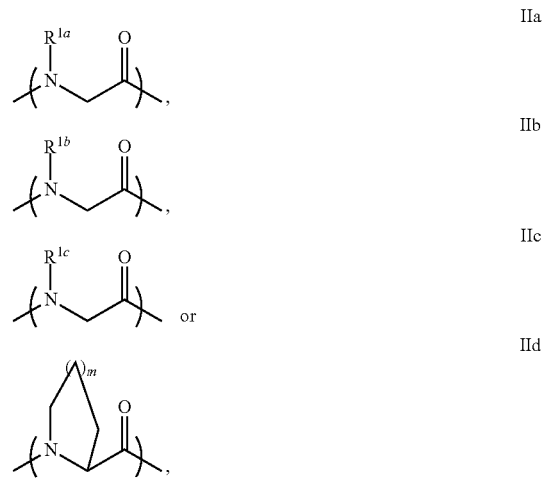

comprised of one or more monomers according to formula IIa, IIb, IIc, or IId:

wherein
each $R^1$ is independently substituted or unsubstituted alkyl;
each $R^2$ is independently hydrogen, or substituted or unsubstituted alkyl; or each $R^1$ and $R^2$ are join together to form a 4-7 membered heterocyclic ring;
each $R^{1a}$ is independently unsubstituted alkyl;
each $R^{1b}$ is independently aminoalkyl, guanidinoalkyl ($H_2N$—C(=NH)—NH-alkyl), or N-containing heteroarylalkyl;
each $R^{1c}$ is independently substituted or unsubstituted aryl, substituted or unsubstituted aralkyl, substituted or unsubstituted heteroarylalkyl, or substituted or unsubstituted diarylalkyl;
each m is 0, 1, 2, or 3;
X is H, or substituted or unsubstituted acyl; Y is $NH_2$, OH, acylamino, or acyloxy;
n is an integer between 2-20, when the peptoid oligomer is of formula Ia; and n is an integer between 4-20, when the peptoid oligomer is of formula Ib;

or a salt thereof; and stereoisomers, isotopic variants and tautomers thereof;

provided that:

i) the peptoid oligomer may comprise one, two, three or all four, IIa, IIb, IIc and IId, of monomers;

ii) at least one of the monomers in the peptoid oligomer is of formula IIb;

iii) each $R^1$ in the peptoid oligomer may be the same or different;

iv) each $R^2$ in the peptoid oligomer may be the same or different; and v) when the peptoid oligomer is of formula Ia and $R^{1b}$ is 4-aminobutyl or 2-imidazol-4-ylethyl, then X is other than H;

or a pharmaceutically acceptable salt, solvate or prodrug thereof; and stereoisomers, isotopic variants and tautomers thereof.

In one aspect, the present invention provides linear peptoid oligomers according to the formula Ia. In one embodiment, with respect to the peptoid oligomers according to the formula Ia, $R^{1b}$ is 4-aminobutyl or 2-imidazol-4-ylethyl, and X is other than H. In another embodiment X is acyl.

In another aspect, the present invention provides cyclic peptoid oligomers according to the formula Ib.

In one embodiment, with respect to peptoid oligomers of formula I, $R^{1b}$ is aminoalkyl.

In one embodiment, with respect to peptoid oligomers of formula I, $R^{1b}$ is aminomethyl, 2-aminoethyl, 3-aminopropyl, 4-aminobutyl, or 6-aminohexyl.

In a further aspect, the present invention provides a method for the preparation of the peptoid oligomers of the invention.

In a further aspect, the peptoid oligomers of the invention may be used to treat microbial or fungal conditions affecting lower animals, and possibly, plants. The peptoid oligomers could be designed and assembled to include the peptoid oligomers pertinent for the treatment of a particular microbe or fungus of interest, and then formulated into appropriate compositions and dosage forms for administration or application to an affected host. Moreover, such compositions may comprise the peptoid oligomers of the invention in mixtures or combinations with other antibiotic agents, such as known antibiotic compounds. In such formulations, the peptoid oligomers of the invention may act synergistically with the known antibiotic compounds, so that the resulting composition demonstrates improved effectiveness.

In a further aspect, the peptoid oligomers of the invention may be used to treat conditions resulting from gram positive and gram negative bacterial strains.

In a further aspect, the peptoid oligomers of the invention may be used to treat various forms of infectious diseases such as Methicillin-resistant *Staphylococcus aureus* (MRSA).

In a further aspect, the present invention provides pharmaceutical compositions comprising a peptoid of the invention, and a pharmaceutical carrier, excipient or diluent. In this aspect of the invention, the pharmaceutical composition can comprise one or more variant peptoid oligomers of the invention, prepared, for example, with a differing array of peptoid linkers, to afford a more comprehensive treatment in the instance where a multiplicity of microbial/viral/fungal antigens are known to be present. Likewise, and as stated above, the pharmaceutical compositions may comprise one or more of the peptoid oligomers of the invention, in combination with other antibiotic agents or compounds, including known antibiotic compounds.

In a further aspect of the invention, a method is disclosed for treating mammals, including humans, as well as lower mammalian species, susceptible to or afflicted with a condition attributable to or resulting from a microbial, viral or fungal infection, which method comprises administering an effective amount of a pharmaceutical composition containing or comprising the peptoid oligomers just described.

In addition to the methods of treatment set forth above, the present invention extends to the use of any of the compounds of the invention for the preparation of medicaments or as medicaments, that may be administered for such treatments, as well as to such compounds for the treatments disclosed and specified.

The present invention also encompasses antimicrobial compositions comprising any of the compounds of the invention, an antimicrobial substrate comprising any of the compounds of the invention, wherein such a compound or compounds are bound to or incorporated into the substrate, and an article comprising an antimicrobial substrate. Such articles include, without limitation, a personal care item, an agricultural item, a cosmetic, a package, a food handling item, a food delivery item, a personal garment, a medical device, a personal hygiene item, an article intended for oral contact, a household item, a toy, or a liquid separation article.

Also encompassed herein are methods for making antimicrobial substrates using the compounds of the invention. The present invention further extends to the use of any of the compounds of the invention for the generation of antimicrobial substrates.

In additional aspects, this invention provides methods for synthesizing the complexes of the invention, with representative synthetic protocols and pathways disclosed later on herein.

Other objects and advantages will become apparent to those skilled in the art from a consideration of the ensuing detailed description, which proceeds with reference to the following illustrative drawings.

DETAILED DESCRIPTION OF THE INVENTION

Definitions

Figure 1:
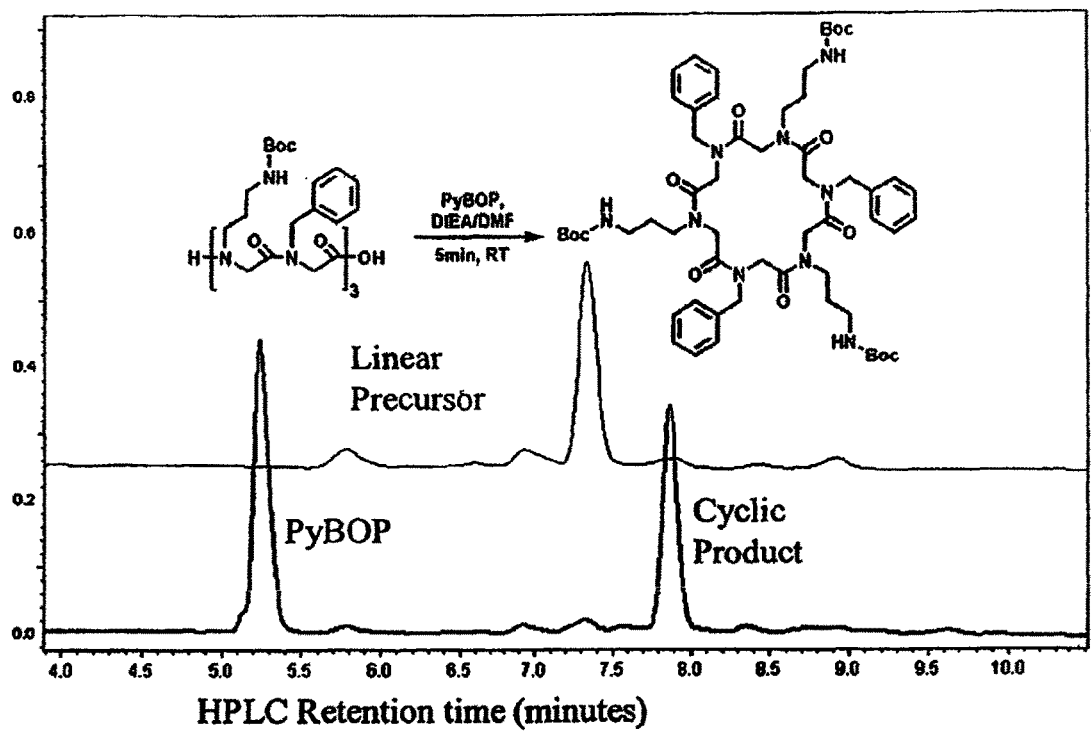
FIG. 1 shows rapid macrocyclization reaction of a representative peptoid hexamer (NapNpm)$_3$ monitored by analytical HPLC (214 nm). Both samples were run in a 10 minute gradient (5%-95% acetonitrile/H$_2$O gradient containing 0.1% TFA). Cyclic products were purified via prep HPLC prior to antimicrobial and hemolytic assays. *Traces shown are of crude compounds, both before and after reaction. Linear precursor was synthesized on solid support and cleaved with 20% HFIP in DCM. Cleavage cocktail was removed under vacuum and cyclization reaction was conducted without purification. Detailed reaction conditions are described in the experimental section.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

N-Substituted Glycine Monomer Designators:
Nap=N-(3-aminopropyl)glycine
Nab=N-(4-aminobutyl)glycine
Nah=N-(6-aminohexyl)glycine
Ngb=N-(4-guanidinobutyl)glycine
Npm=N-(phenylmethyl)glycine
Nnm=N-(naphthylmethyl)glycine
Ndp=N-(2,2-diphenylethyl)glycine
Nip=N-(isopropyl)glycine
Nib=N-(isobutyl)glycine N-Substituted Glycine Monomer Designators:

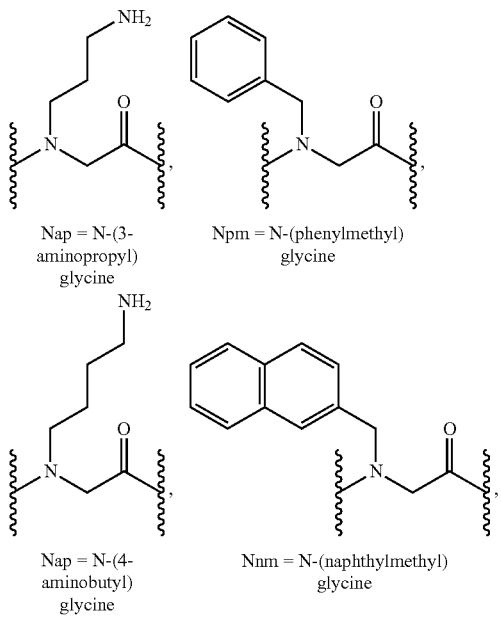

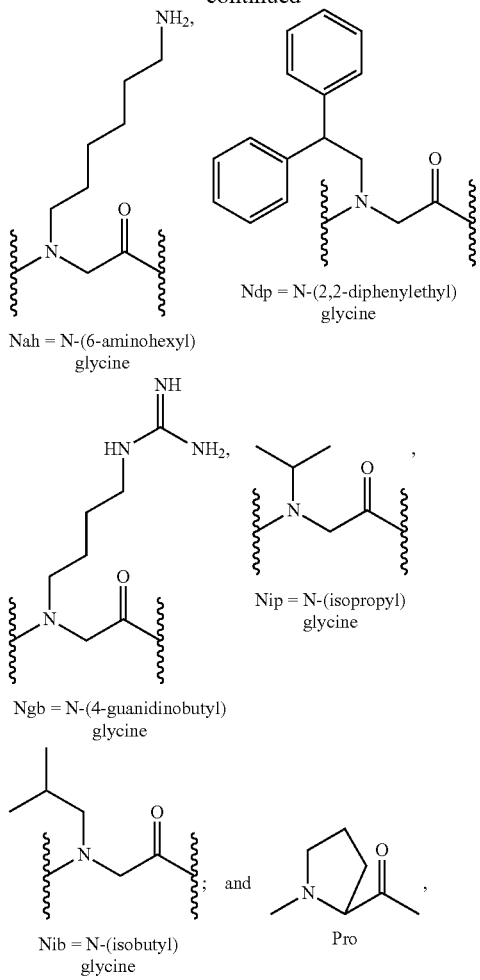

'Acyl' or 'Alkanoyl' refers to a radical —C(O)R$^{20}$, where R$^{20}$ is hydrogen, C$_1$-C$_8$ alkyl, C$_3$-C$_{10}$ cycloalkyl, C$_3$-C$_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently
C$_1$-C$_8$ alkyl, substituted with halo or hydroxy; or
C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Alkoxy' refers to the group —OR$^{29}$ where R$^{29}$ is C$_1$-C$_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl, n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and iso-amyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R'', —SO$_2$NR''R''', —C(O)R'', —C(O)OR'', —OC(O)R'', —NR'''C(O)R'', —C(O)NR''R''', —NR''R''', or —(CR'''R'''')$_m$OR'''; wherein each R'' is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted haloalkoxy or hydroxy. Each of R''' and R'''' independently represents H or C$_1$-C$_8$ alkyl.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_1$ alkyl, halo, cyano, unsubstituted alkoxy, unsubstituted haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

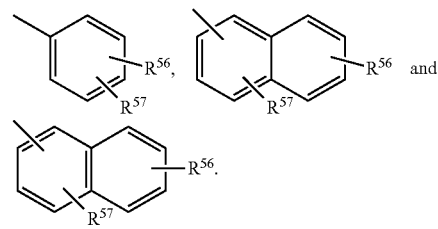

In these formulae one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocycloalkyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O or S. R$^{60}$ and R$^{61}$ are independently hydrogen, C1-C8 alkyl, C1-C4 haloalkyl, C3-C10 cycloalkyl, 4-10 membered heterocycloalkyl, C6-C10 aryl, substituted aryl, 5-10 membered heteroaryl.

'Heteroaryl' means an aromatic ring structure, monocyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

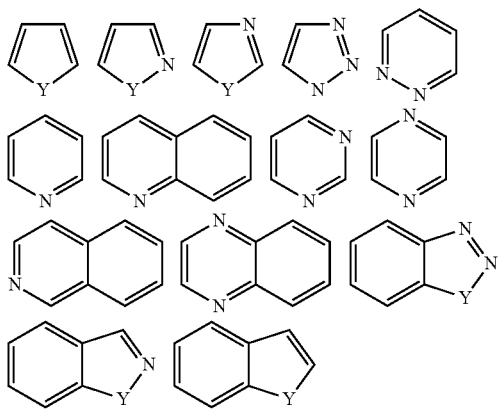

wherein each Y is selected from carbonyl, N, NR$^{65}$, O and S; and R$^{65}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

Examples of representative aryl having hetero atoms containing substitution include the following:

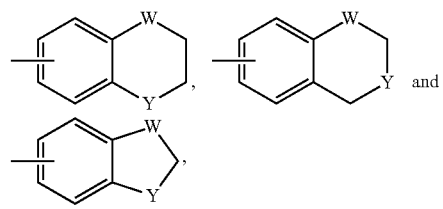

wherein each W is selected from C(R$^{66}$)$_2$, NR$^{66}$, O and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

"Unnatural amino acids" means amino acids and corresponding peptoid oligomers that are synthesized from single amino acid starting materials. Such unnatural amino acids may be prepared and used individually in accordance with the present invention, or may be incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, *Science,* 244: 182-188 (April 1989).

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "patient" and "subject" are used interchangeably herein. Accordingly, a subject can be a mammal, in a particular embodiment a human, or a bird, a reptile, an amphibian, or a plant.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2H$ or D), carbon-13 ($^{13}C$), nitrogen-15 ($^{15}N$), or the like. It will be understood that, in a compound comprising an unnatural proportion of an isotope, any example of an atom where present, may vary in isotope composition. For example, any hydrogen may be $^2H/D$, or any carbon may be $^{13}C$, or any nitrogen may be $^{15}N$, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The Peptoid Oligomers

As set forth earlier herein, the linear glycine peptoids and glycine peptoid macrocycles of the present invention comprise antimicrobial/antiviral/antifungal linear peptoids and cyclic peptoids. Accordingly, the compounds may be linear peptoids or cyclic peptoids and may have a lethal effect on bacteria, viruses, or fungi. More particularly, the linear or cyclic peptoids may be any antimicrobial linear or cyclic peptoids, or fragments thereof, natural cyclic peptoids, and any synthetic analogs or de novo designs. These cyclic and linear peptoids can accordingly include nonnatural amino acids: beta-amino acids, d-amino acids and/or non-indigenous amino acids.

Peptoids exhibit many advantageous characteristics for development of bioactive compounds, as they are amenable to efficient solid phase synthesis; can incorporate highly diverse chemical functionalities; can establish a relationship between oligomer sequence, three-dimensional structure, and function; do not require the presence of chiral centers; can demonstrate marked resistance to degradation; have superior cell permeability characteristics relative to peptides; and can manifest rapid cytotoxicities. Some of the advantageous properties of peptidomimetics for use as antibiotics are described in Srinivas et al. (*Science* 2010, 327, 1010-1013), which is incorporated herein in its entirety.

With respect to cyclic peptoids of the invention, the present inventors are the first researchers to generate cyclic peptoids. Many previous attempts at making cyclic peptoids by skilled practitioners had failed. Consequently, the perception of skilled practitioners in the field was that the likelihood of success in such an endeavor was limited at best.

More particularly, the present invention relates to peptoid oligomers having antimicrobial properties, according to formula Ia or Ib:

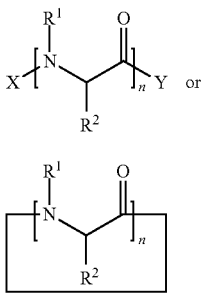

Ia

Ib comprised of one or more monomers according to formula IIa, IIb, IIc, or IId:

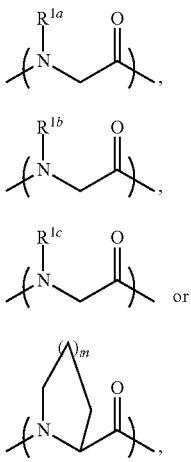

IIa

IIb

IIc

IId wherein each $R^1$ is independently substituted or unsubstituted alkyl;

each $R^2$ is independently hydrogen, or substituted or unsubstituted alkyl; or each $R^1$ and $R^2$ are join together to form a 4-7 membered heterocyclic ring;

each $R^{1a}$ is independently unsubstituted alkyl;

each $R^{1b}$ is independently aminoalkyl, guanidinoalkyl ($H_2N-C(=NH)-NH$-alkyl), or N-containing heteroarylalkyl;

each $R^{1c}$ is independently substituted or unsubstituted aryl, substituted or unsubstituted aralkyl, substituted or unsubstituted heteroarylalkyl, or substituted or unsubstituted diarylalkyl;

each m is 0, 1, 2, or 3;

X is H, or substituted or unsubstituted acyl; Y is $NH_2$, OH, acylamino, or acyloxy;

n is an integer between 2-20, when the peptoid oligomer is of formula Ia; and n is an integer between 4-20, when the peptoid oligomer is of formula Ib;

or a salt thereof; and stereoisomers, isotopic variants and tautomers thereof;

provided that:
i) the peptoid oligomer may comprise one, two, three or all four, IIa, IIb, IIc and IId, of monomers;
ii) at least one of the monomers in the peptoid oligomer is of formula IIb;
iii) each $R^1$ in the peptoid oligomer may be the same or different;
iv) each $R^2$ in the peptoid oligomer may be the same or different; and
v) when the peptoid oligomer is of formula Ia and $R^{1b}$ is 4-aminobutyl or 2-imidazol-4-ylethyl, then X is other than H;

or a pharmaceutically acceptable salt, solvate or prodrug thereof; and stereoisomers, isotopic variants and tautomers thereof.

In one embodiment, with respect to peptoid oligomers of formula Ia or Ib, $R^h$ is unsubstituted alkyl.

In one embodiment, with respect to peptoid oligomers of formula Ia or Ib, $R^{1a}$ is alkyl, substituted with halo, hydroxy, amino, nitro, and alkoxy.

In another embodiment, with respect to peptoid oligomers of formula Ia or Ib, $R^{1a}$ is alkyl, substituted with halo. In one particular embodiment, $R^{1a}$ is alkyl, substituted with F. In another particular embodiment, $R^{1a}$ is alkyl, substituted with one or more F.

In one embodiment, with respect to peptoid oligomers of formula Ia or Ib, $R^{1a}$ is Me, Et, n-Pr, i-Pr, n-Bu, sec-Bu, or i-Bu.

In one embodiment, with respect to peptoid oligomers of formula Ia or Ib, $R^{1c}$ is benzyl, unsubstituted or substituted with one or more groups selected from alkyl, halo, hydroxy, amino, nitro, and alkoxy.

In one embodiment, with respect to peptoid oligomers of formula Ia or Ib, $R^{1c}$ is phenyl, unsubstituted or substituted with one or more groups selected from alkyl, halo, hydroxy, amino, nitro, and alkoxy.

In one embodiment, with respect to peptoid oligomers of formula Ia or Ib, $R^{1c}$ is phenyl, substituted with one or more halo. In one particular embodiment, with respect to peptoid oligomers of formula Ia or Ib, $R^{1c}$ is phenyl, substituted with one or more F.

In one embodiment, with respect to peptoid oligomers of formula Ia or Ib, is unsubstituted phenyl.

In one embodiment, with respect to peptoid oligomers of formula Ia or Ib, $R^{1c}$ is naphthyl, unsubstituted or substituted with one or more groups selected from alkyl, halo, hydroxy, amino, nitro, and alkoxy.

In one embodiment, with respect to peptoid oligomers of formula Ia or Ib, $R^{1c}$ is unsubstituted naphthyl.

In one embodiment, with respect to peptoid oligomers of formula Ia or Ib, $R^{1c}$ is naphthyl, substituted with one or more halo. In one particular embodiment, with respect to peptoid oligomers of formula Ia or Ib, $R^{1c}$ is naphthyl, substituted with one or more F.

In one embodiment, with respect to peptoid oligomers of formula Ia or Ib, $R^{1c}$ is phenethyl, unsubstituted or substituted with one or more groups selected from alkyl, halo, hydroxy, amino, nitro, and alkoxy.

In one embodiment, with respect to peptoid oligomers of formula Ia or Ib, $R^{1c}$ is phenethyl, substituted with one or more halo. In one particular embodiment, with respect to peptoid oligomers of formula Ia or Ib, $R^{1c}$ is phenethyl, substituted with one or more F.

In one embodiment, with respect to peptoid oligomers of formula Ia or Ib, $R^{1c}$ is 2-naphthyl, unsubstituted or substituted with one or more groups selected from alkyl, halo, hydroxy, amino, nitro, and alkoxy. In one particular embodiment, $R^{1c}$ is 2-naphthyl, substituted with one or more F.

In one embodiment, with respect to peptoid oligomers of formula Ia or Ib, $R^{1c}$ is 2,2-diphenylethyl, unsubstituted or substituted with one or more groups selected from alkyl, halo, hydroxy, amino, nitro, and alkoxy. In one particular embodiment, $R^{1c}$ is 2,2-diphenylethyl, substituted with one or more F.

In one embodiment, with respect to peptoid oligomers of formula Ia or Ib, $R^{1c}$ is furanyl or thienyl, unsubstituted or substituted with one or more groups selected from alkyl, halo, hydroxy, amino, nitro, and alkoxy. In one particular embodiment, $R^{1c}$ is furanyl or thienyl, substituted with one or more F.

In one embodiment, with respect to peptoid oligomers of formula Ia or Ib, m is 1 or 2.

In one embodiment, with respect to peptoid oligomers of formula Ia or Ib, m is 1.

In one embodiment, with respect to peptoid oligomers of formula Ia or Ib, $R^{1b}$ is aminomethyl, 2-aminoethyl, 3-aminopropyl, 4-aminobutyl, 5-aminopentyl, or 6-aminohexyl.

In one embodiment, with respect to peptoid oligomers of formula Ia or Ib, $R^{1b}$ is aminomethyl, 2-aminoethyl, 3-aminopropyl, 4-aminobutyl, 5-aminopentyl, or 6-aminohexyl; and wherein the aminoalkyl groups (aminomethyl, 2-aminoethyl, 3-aminopropyl, 4-aminobutyl, 5-aminopentyl, or 6-aminohexyl) may be substituted with one or more F.

In one embodiment, with respect to peptoid oligomers of formula Ia or Ib, $R^{1b}$ is 3-aminopropyl.

In one embodiment, with respect to peptoid oligomers of formula Ia or Ib, $R^{1b}$ is guanidinoalkyl.

In one embodiment, with respect to peptoid oligomers of formula Ia or Ib, $R^{1b}$ is guanidinomethyl, 2-guanidinoethyl, 3-guanidinopropyl, 4-guanidinobutyl, 5-guanidinopentyl, or 6-guanidinohexyl.

In one embodiment, with respect to peptoid oligomers of formula Ia or Ib, $R^{1b}$ is guanidinomethyl, 2-guanidinoethyl, 3-guanidinopropyl, 4-guanidinobutyl, 5-guanidinopentyl, or 6-guanidinohexyl; and wherein the guanidinoalkyl groups may be substituted with one or more F.

In one embodiment, with respect to peptoid oligomers of formula Ia or Ib, $R^{1b}$ is 4-guanidinobutyl.

In one embodiment, with respect to peptoid oligomers of formula Ia or Ib, $R^{1b}$ is imidazolylmethyl, 2-imidazolylethyl, 3-imidazolylpropyl, 4-imidazolylbutyl, 5-imidazolylpentyl, or 6-imidazolylhexyl.

In one embodiment, with respect to peptoid oligomers of formula Ia or Ib, $R^{1b}$ is imidazolylmethyl, 2-imidazolylethyl, 3-imidazolylpropyl, 4-imidazolylbutyl, 5-imidazolylpentyl, or 6-imidazolylhexyl; and wherein the imidazoalkyl groups may be substituted with one or more F In one embodiment, with respect to peptoid oligomers of formula Ia or Ib, $R^{1b}$ is methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one embodiment, with respect to peptoid oligomers of formula Ia or Ib, $R^{1b}$ is methyl, n-propyl, n-butyl, n-pentyl, and n-hexyl, substituted with pyrrolyl, oxazolyl, isoxazolyl, thiazolyl, thiadiazolyl, triazolyl, or tetrazolyl; and all these groups are substituted with one or more F.

In one embodiment, with respect to peptoid oligomers of formula Ia or Ib, n is 6, 8 or 10.

In one embodiment, with respect to peptoid oligomers of formula Ia or Ib, the peptoid oligomer is according to formula Ia; X is H, and $R^{1b}$ is other than 4-aminobutyl or 2-imidazol-4-ylethyl.

In one embodiment, with respect to peptoid oligomers of formula Ia or Ib, the peptoid oligomer is according to formula Ia; X is acyl, and $R^{1b}$ is 4-aminobutyl or 2-imidazol-4-ylethyl.

In one embodiment, with respect to peptoid oligomers of formula Ia or Ib, the peptoid oligomer is according to formula Ia; and X is acyl.

In one embodiment, with respect to peptoid oligomers of formula Ia or Ib, the peptoid oligomer is according to formula Ia; and X is acyl; and 'acyl' refers to a radical —C(O)$R^{20}$, where $R^{20}$ is $C_1$-$C_{30}$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. In one particular embodiment X is acetyl, cyclohexylcarbonyl, cyclohexylmethylcarbonyl, benzoyl or benzylcarbonyl. In another particular embodiment X is —C(O)—$C_1$-$C_{20}$ alkyl, —C(O)—($CH_2$)$_t$($C_6$-$C_{10}$ aryl), —C(O)—($CH_2$)$_t$(5-10 membered heteroaryl), —C(O)—($CH_2$)$_t$($C_3$-$C_{10}$ cycloalkyl), and —C(O)—($CH_2$)$_t$(4-10 membered heterocycloalkyl), wherein t is an integer from 0 to 4.

In one embodiment, with respect to peptoid oligomers of formula Ia or Ib, the peptoid oligomer is according to formula Ia; and X is acyl; and 'acyl' refers to a radical —C(O)$R^{20}$, where $R^{20}$ is Me, Et, n-Pr, i-Pr, n-Bu, i-Bu, pentyl, hexyl, heptyl, octyl, nonyl, or decyl.

In one embodiment, with respect to peptoid oligomers of formula Ia or Ib, the peptoid oligomer is according to formula Ia; and X is acyl; and 'acyl' refers to a radical —C(O)$R^{20}$, where $R^{20}$ is $C_{11}$-$C_{20}$ alkyl.

In one embodiment, with respect to peptoid oligomers of formula Ia or Ib, the peptoid oligomer is according to formula Ia; and X is lauroyl, tridecanoyl, myristoyl, pentadecanoyl, palmitoyl, or cetoyl.

In one embodiment, with respect to peptoid oligomers of formula Ia or Ib, the peptoid oligomer is according to formula Ia; and X is acyl; and 'acyl' refers to a radical —C(O)$R^{20}$, where $R^{20}$ is $C_3$-$C_{10}$ cycloalkyl. In another embodiment, $R^{20}$ is cyclopropyl, cyclobutyl, cyclopentyl or cyclohexyl.

In one embodiment, with respect to peptoid oligomers of formula Ia or Ib, the peptoid oligomer is according to formula Ia; and X is acyl; and 'acyl' refers to a radical —C(O)$R^{20}$, where $R^{20}$ is —($CH_2$)$_t$($C_3$-$C_{10}$ cycloalkyl), and t is 1, 2, or 3. In another embodiment $R^{20}$ is —$CH_2$—($C_3$-$C_{10}$ cycloalkyl). In yet another embodiment $R^{20}$ is cyclopropylmethyl or cyclobutylmethyl.

In yet another embodiment, with respect to peptoid oligomers of formula Ia or Ib, the peptoid oligomer is according to formula Ia; and X is acyl, unsubstituted or substituted with cycloalkyl, or phenyl.

In yet another embodiment, with respect to peptoid oligomers of formula Ia or Ib, the peptoid oligomer is according to formula Ia; and X is acetyl, lauroyl, tridecanoyl, myristoyl, pentadecanoyl, palmitoyl, caproyl, benzoyl, cetyl, decyl, acetyl, phenyl acetyl, cyclohexyl acetyl, or valeroyl.

In yet another embodiment, with respect to peptoid oligomers of formula Ia or Ib, the peptoid oligomer is according to formula Ia; and X is acetyl, or palmitoyl.

In yet another embodiment, with respect to peptoid oligomers of formula Ia or Ib, the peptoid oligomer is according to formula Ia; and X is glucuronyl residue.

In one embodiment, with respect to peptoid oligomers of formula Ia or Ib, the peptoid oligomer is according to formula Ia; and Y is $NH_2$.

In one embodiment, with respect to peptoid oligomers of formula Ia or Ib, the peptoid oligomer is according to formula Ib.

In one embodiment, with respect to peptoid oligomers of formula Ia or Ib, n is 6; and the peptoid oligomer consists of three units of monomer IIb; and three units of monomer IIc.

In one embodiment, with respect to peptoid oligomers of formula Ia or Ib, n is 6; and the peptoid oligomer consists of two units of monomer IIb; and four units of monomer IIc.

In one embodiment, with respect to peptoid oligomers of formula Ia or Ib, n is 6; and the peptoid oligomer consists of four units of monomer IIb; and two units of monomer IIc.

In one embodiment, with respect to peptoid oligomers of formula Ia or Ib, n is 8; and the peptoid oligomer consists of four units of monomer IIb; and four units of monomer IIc.

In one embodiment, with respect to peptoid oligomers of formula Ia or Ib, n is 10; and the peptoid oligomer consists of five units of monomer IIb; and five units of monomer IIc.

In one embodiment, with respect to peptoid oligomers of formula Ia or Ib, $R^{1b}$ is 3-aminopropyl, 4-aminobutyl, or 6-aminohexyl.

In one embodiment, with respect to peptoid oligomers of formula Ia or Ib, $R^{1b}$ is 4-guanidinobutyl.

In one embodiment, with respect to peptoid oligomers of formula Ia or Ib, $R^{1c}$ is benzyl.

In one embodiment, with respect to peptoid oligomers of formula Ia or Ib, $R^{1c}$ is 2-naphthyl.

In one embodiment, with respect to peptoid oligomers of formula Ia or Ib, $R^{1c}$ is 2,2-diphenylethyl.

In one embodiment, with respect to peptoid oligomers of formula Ia or Ib, the peptoid oligomer is according to formula Ia; X is acyl; and Y is $NH_2$.

In one embodiment, with respect to peptoid oligomers of formula Ia or Ib, the peptoid oligomer is according to formula Ib.

In one embodiment, with respect to peptoid oligomers of formula Ia or Ib, the said peptoid oligomer consists of one or more monomers selected from Nap, Nab, Nah, Ngb, Npm, Nnm, Ndp, Nip, Nib, and Pro:

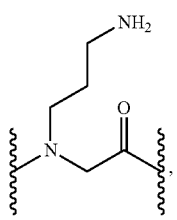

Nap = N-(3-aminopropyl) glycine

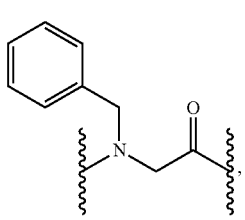

Npm = N-(phenylmethyl) glycine

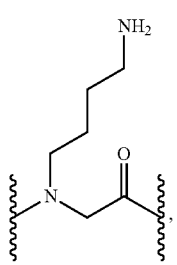

Nap = N-(4-aminobutyl) glycine

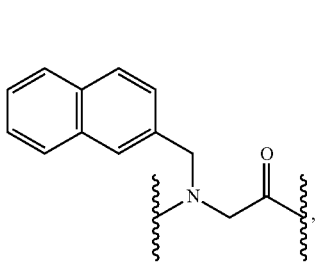

Nnm = N-(naphthylmethyl) glycine

-continued

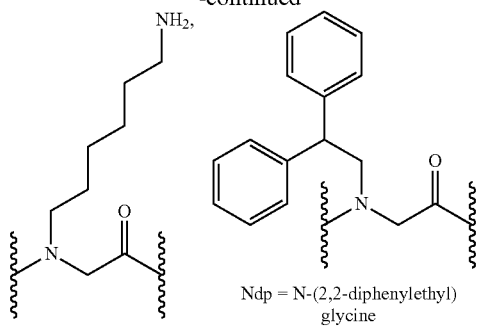

Nah = N-(6-aminohexyl) glycine

Ndp = N-(2,2-diphenylethyl) glycine

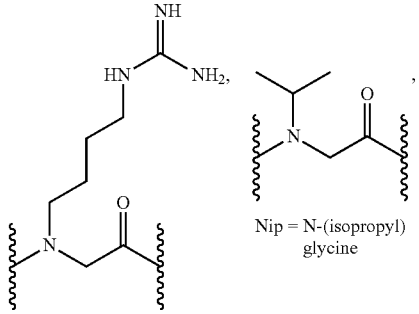

Ngb = N-(4-guanidinobutyl) glycine

Nip = N-(isopropyl) glycine

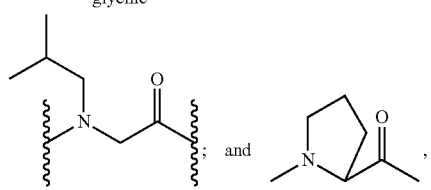

Nib = N-(isobutyl) glycine

Pro provided that at least one of the monomers in the peptoid oligomer is Nap, Nab, Nah, or Ngb.

In one embodiment, with respect to peptoid oligomers of formula Ia or Ib, n is 6; and the said peptoid oligomer consists of three Ngb, Nah, Nap, or Nab monomers; and three Ndp, Nnm, or Npm, monomers.

In one embodiment, with respect to peptoid oligomers of formula Ia or Ib, n is 6; and the said peptoid oligomer consists of four Nap monomers; and two Npm monomers.

In one embodiment, with respect to peptoid oligomers of formula Ia or Ib, n is 6; and the said peptoid oligomer consists of four Npm monomers; and two Nap monomers.

In one embodiment, with respect to peptoid oligomers of formula Ia or Ib, n is 6; and the said peptoid oligomer consists of four Ndp monomers; and two Ngb monomers.

In one embodiment, with respect to peptoid oligomers of formula Ia or Ib, n is 8; and the said peptoid oligomer consists of four Nap monomers; and four Npm monomers.

In one embodiment, with respect to peptoid oligomers of formula Ia or Ib, n is 10; and the said peptoid oligomer consists of two Nip monomers; two Nap monomers; two Nib monomers; two NpmPro monomers; and two Pro monomers.

In one embodiment, with respect to peptoid oligomers of formula Ia or Ib, n is 10; and the said peptoid oligomer consists of two Ndp monomers; two Nib monomers; two Ngb monomers; two Nip monomers; and two Pro monomers.

In one embodiment, with respect to peptoid oligomers of formula Ia or Ib, n is 10; and the said peptoid oligomer consists of two Npm monomers; two Nib monomers; two Nap monomers; two NipPro monomers; and two Pro monomers.

In one embodiment, with respect to peptoid oligomers of formula Ia or Ib, n is 10; and the said peptoid oligomer consists of five Nap monomers; and five Npm monomers.

In one embodiment, with respect to peptoid oligomers of formula Ia or Ib, n is 10; and the said peptoid oligomer consists of five Ngb monomers; and five Ndp monomers.

In one embodiment, with respect to peptoid oligomers of formula Ia or Ib, the peptoid oligomer is according to formula Ia; X is acyl; and Y is $NH_2$.

In one embodiment, with respect to peptoid oligomers of formula Ia or Ib, the peptoid oligomer is according to formula Ib.

In one embodiment, with respect to peptoid oligomers of formula Ia or Ib, Ac is acetyl or MeCO; and the peptoid oligomer is according to formula Ia.

In one embodiment, with respect to peptoid oligomers of formula Ia or Ib, C is cyclic; and the peptoid oligomer is according to formula Ib.

In one embodiment, with respect to peptoid oligomers of formula Ia or Ib, Ac is acetyl or MeCO; and the peptoid oligomer is according to formula Ia.

In one embodiment, with respect to peptoid oligomers of formula Ia or Ib, C is cyclic; and the peptoid oligomer is according to formula Ib.

In one embodiment, with respect to peptoid oligomers of formula Ia, the peptoid oligomer is selected from the group consisting of:
Acyl(NgbNpm)$_3$NH$_2$;
Acyl(NahNpm)$_3$NH$_2$;
Acyl(NapNdp)$_3$NH$_2$;
Acyl(NapNnm)$_3$NH$_2$;
Acyl(NapNpm)$_2$Nap$_2$NH$_2$;
Acyl(NapNpm)$_3$NH$_2$;
Acyl(NapNpm)$_4$NH$_2$;
Acyl(NapNpm)$_5$NH$_2$;
Acyl(NpmNap)$_2$Npm$_2$NH$_2$;
Acyl(NipNapNibNpmPro)$_2$NH$_2$;
Acyl(NdpNibNgbNipPro)$_2$NH$_2$;
Acyl(NpmNibNapNipPro)$_2$NH$_2$;
Acyl(NabNpm)$_3$NH$_2$;
Acyl(NgbNdp)$_5$NH$_2$; and
Acyl(NdpNgb)$_2$Ndp$_2$NH$_2$;
wherein "acyl" is as described above.

In one embodiment, 'acyl' refers to a radical —C(O)R$^{20}$, where R$^{20}$ is C$_1$-C$_{30}$ alkyl, C$_3$-C$_{10}$ cycloalkyl, C$_3$-C$_{10}$ cycloalkylmethyl, 4-10 membered heterocycloalkyl, aryl, arylalkyl, 5-10 membered heteroaryl or heteroarylalkyl as defined herein. In one particular embodiment "acyl" is acetyl, cyclohexylcarbonyl, cyclohexylmethylcarbonyl, benzoyl or benzylcarbonyl. In another particular embodiment "acyl" is —C(O)—C$_1$-C$_{20}$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$ (410 membered heterocycloalkyl), wherein t is an integer from 0 to 4.

In one embodiment, 'acyl' refers to a radical —C(O)R$^{20}$, where R$^{20}$ is Me, Et, n-Pr, i-Pr, n-Bu, i-Bu, pentyl, hexyl, heptyl, octyl, nonyl, or decyl.

In one embodiment, 'acyl' refers to a radical —C(O)R$^{20}$, where R$^{20}$ is C$_{11}$-C$_{20}$ alkyl.

In one particular embodiment, "acyl" is lauroyl, tridecanoyl, myristoyl, pentadecanoyl, palmitoyl, or cetoyl.

In one embodiment, 'acyl' refers to a radical —C(O)R$^{20}$, where R$^{20}$ is C$_3$-C$_{10}$ cycloalkyl. In another embodiment, R$^{20}$ is cyclopropyl, cyclobutyl, cyclopentyl or cyclohexyl.

In one embodiment, 'acyl' refers to a radical —C(O)R$^{20}$, where R$^{20}$ is —(CH$_2$)$_t$(C$_3$-C$_{10}$ cycloalkyl), and t is 1, 2, or 3. In another embodiment R$^{20}$ is —CH$_2$—(C$_3$-C$_{10}$ cycloalkyl). In yet another embodiment R$^{20}$ is cyclopropylmethyl or cyclobutylmethyl.

In yet another embodiment, "acyl" is acetyl unsubstituted or substituted with cycloalkyl, or phenyl.

In yet another embodiment, "acyl" is acetyl, lauroyl, tridecanoyl, myristoyl, pentadecanoyl, palmitoyl, caproyl, benzoyl, cetyl, decyl, acetyl, phenyl acetyl, cyclohexyl acetyl, or valeroyl.

In yet another embodiment, "acyl" is acetyl, or palmitoyl.

In yet another embodiment, "acyl" is glucuronyl residue.

In most particular embodiment, "acyl" is acetyl or MeCO—.

In one embodiment, with respect to peptoid oligomers of formula Ia, the peptoid oligomer is selected from the group consisting of:
Ac(NgbNpm)$_3$NH$_2$;
Ac(NahNpm)$_3$NH$_2$;
Ac(NapNdp)$_3$NH$_2$;
Ac(NapNnm)$_3$NH$_2$;
Ac(NapNpm)$_2$Nap$_2$NH$_2$;
Ac(NapNpm)$_3$NH$_2$;
Ac(NapNpm)$_4$NH$_2$;
Ac(NapNpm)$_5$NH$_2$;
Ac(NpmNap)$_2$Npm$_2$NH$_2$;
Ac(NipNapNibNpmPro)$_2$NH$_2$;
Ac(NdpNibNgbNipPro)$_2$NH$_2$;
Ac(NpmNibNapNipPro)$_2$NH$_2$;
Ac(NabNpm)$_3$NH$_2$;
Ac(NgbNdp)$_5$NH$_2$; and
Ac(NdpNgb)$_2$Ndp$_2$NH$_2$;
wherein Ac is acetyl or MeCO.

In one embodiment, with respect to peptoid oligomers of formula Ib, the peptoid oligomer is selected from the group consisting of:
C(NgbNpm)$_3$;
C(NahNpm)$_3$;
C(NapNdp)$_3$;
C(NapNnm)$_3$;
C(NapNpm)$_2$Nap$_2$;
C(NapNpm)$_3$;
C(NapNpm)$_4$;
C(NapNpm)$_5$;
C(NpmNap)$_2$Npm$_2$;
C(NipNapNibNpmPro)$_2$;
C(NdpNibNgbNipPro)$_2$;
C(NpmNibNapNipPro)$_2$;
C(NabNpm)$_3$;
C(NgbNdp)$_5$; and
C(NdpNgb)$_2$Ndp$_2$
wherein C is cyclic.

In one embodiment, with respect to peptoid oligomers of formula Ia, the peptoid oligomer is selected from the group consisting of:
Ac(NapNdp)$_3$NH$_2$;
Ac(NapNpm)$_3$NH$_2$; and
Ac(NapNpm)$_5$NH$_2$;
wherein Ac is acetyl or MeCO.

In one embodiment, with respect to peptoid oligomers of formula Ia or Ib, the peptoid oligomer is selected from the group consisting of:

C(NapNdp)₃;

C(NapNpm)₃; and

C(NapNpm)₅;

wherein C is cyclic.

In one embodiment, with respect to peptoid oligomers of formula Ia or Ib, the peptoid oligomer is selected from the oligomers listed in Table 1, provided the compound or oligomer is not ID #1 and #17.

In one embodiment, with respect to peptoid oligomers of formula Ia or Ib, the peptoid oligomer is any one of oligomers or compounds with IDs 2-16 and 18-32 as listed in Table 1.

In one embodiment, with respect to peptoid oligomers of formula Ib, the peptoid oligomer is selected from

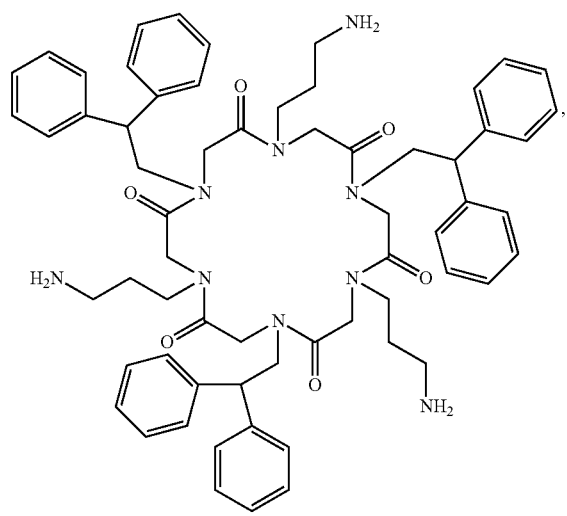

Molecular Weight: 1054.33

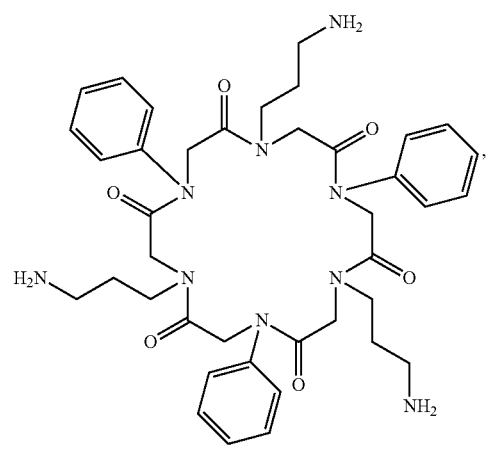

Molecular Weight: 741.88

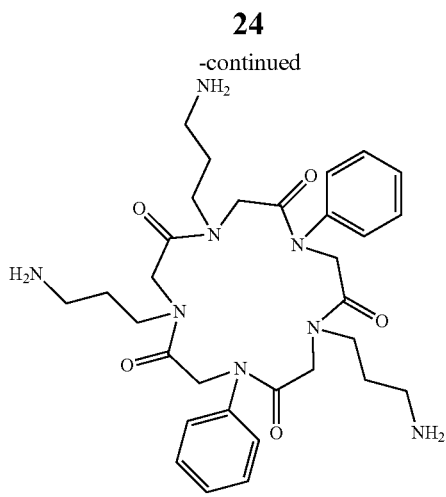

Molecular Weight: 608.73

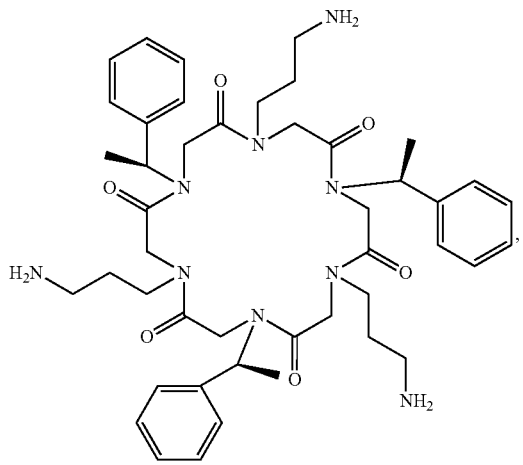

Molecular Weight: 826.04

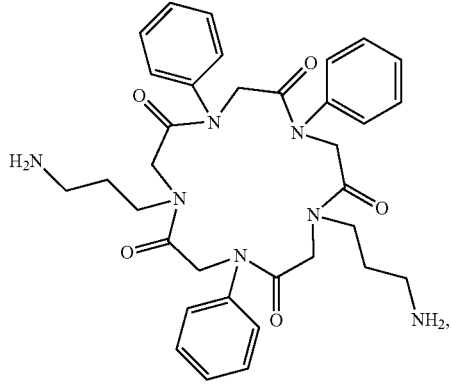

Molecular Weight: 672.73

-continued

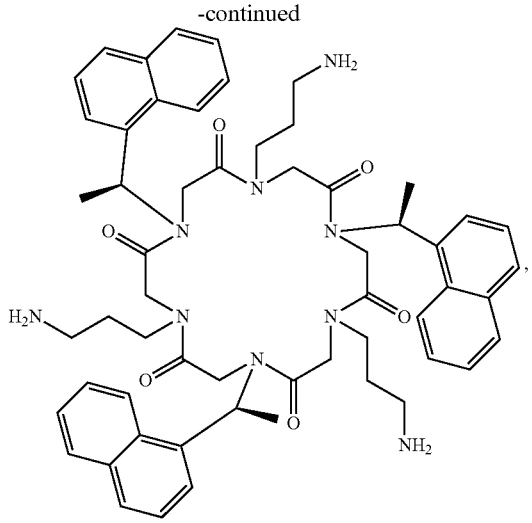

Molecular Weight: 976.21

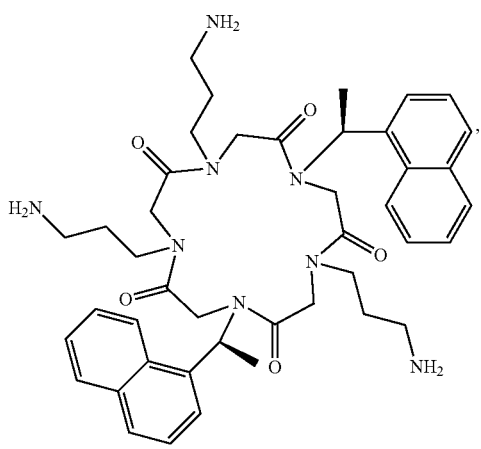

Molecular Weight: 764.96

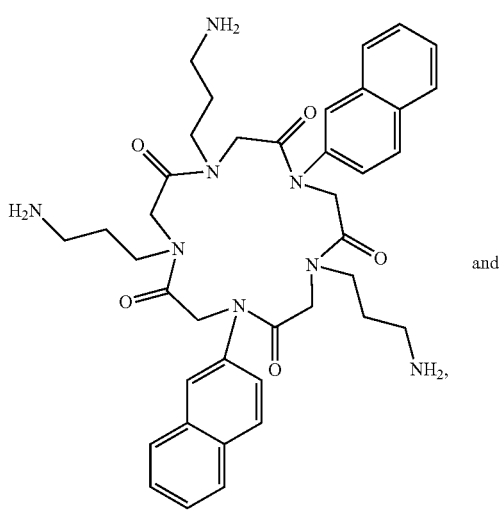

and

Molecular Weight: 708.85

-continued

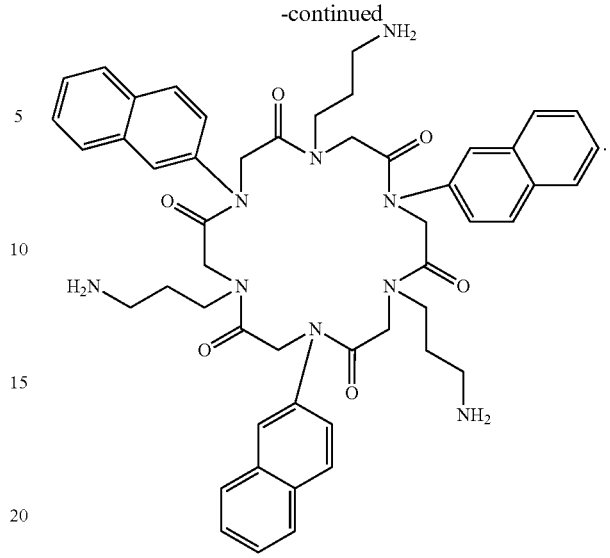

Molecular Weight: 892.05

In one aspect of the invention, the peptoid oligomer is linear or of formula Ia.

In one aspect of the invention, the peptoid oligomer is cyclic or of formula Ib.

In one particular embodiment, with respect to peptoid oligomers of formula Ia or Ib, the alkyl and aryl groups specified herein may further be substituted with one or more F.

In certain aspects and where appropriate, the present invention extends to the preparation of prodrugs and derivatives of the peptoids of the invention. Prodrugs are derivatives which have cleavable groups and become by solvolysis or under physiological conditions the peptoid of the invention, which are pharmaceutically active, in vivo.

In one embodiment, the invention provides a pharmaceutical composition comprising a pharmaceutically acceptable carrier and a pharmaceutically effective amount of the peptoid of formula Ia and/or Ib.

In one embodiment, the invention provides a pharmaceutical composition of the peptoid of formula Ia and/or Ib, comprising a pharmaceutically acceptable carrier, and the carrier is a parenteral carrier, oral or topical carrier.

In one embodiment, the invention provides a method for preventing, treating, ameliorating or managing a disease or condition which comprises administering to a patient in need of such prevention, treatment, amelioration or management, a prophylactically or therapeutically effective amount of the pharmaceutical composition of the peptoid of formula Ia and/or Ib.

In one embodiment, the disease or condition is or results from a bacterial infection.

In one embodiment, the disease or condition is or results from gram positive or gram negative bacterial strains. The compositions of the present invention can be used to kill or inhibit the growth of any of the following microbes or mixtures of the following microbes, or, alternatively, can be administered to treat local and/or systemic microbial infections or illnesses caused by the following microbes or mixtures of the following microbes: Gram-positive cocci, for example Staphylococci (*Staph. aureus, Staph. epidermidis*) and Streptococci (*Strept. agalactiae, Strept. faecalis, Strept. pneumoniae, Strept. pyogenes*); Gram-negative cocci (*Neisseria gonoirhoeae* and *Yersinia pestis*) and Gram-negative rods such as Enterobacteriaceae, for example *Escherichia coli, Hamophilus influenzae, Citrobacter* (*Citrob. freundii, Citrob. divernis*), *Salmonella* and *Shigella*, and *Francisella* (*Francisella tularensis*); Gram-positive rods such as *Bacillus* (*Bacillus anthracis, Bacillus thuringenesis*); furthermore *Klebsiella* (*Klebs. pneumoniae, Klebs. oxytoca*), *Enterobacter* (*Ent. aerogenes, Ent. agglomerans*), *Hafnia, Serratia* (*Serr. marcescens*), *Proteus* (*Pr. mirabilis, Pr. rettgeri, Pr. vulgaris*), *Providencia, Yersinia*, the genus *Acinetobacter*, and the genus *Brevibacterium*, including *Brevibacterium* linens, which is ubiquitously present on human skin and is the causative agent of foot odor. Furthermore, the antimicrobial spectrum of the peptoid oligomers of the present invention covers the genus *Pseudomonas* (*Ps. aeruginosa, Ps. maltophilia*), the aerotolerant anaerobic gram positive bacterium *Propionibacterium acnes* (*P. acnes*), which is causatively linked to skin acne, and strictly anaerobic bacteria such as, for example, *Bacteroides fragilis*, representatives of the genus *Peptococcus, Peptostreptococcus* and the genus *Clostridium*; furthermore Mycoplasmas (*M. pneumoniae, M. hominis, Ureaplasma urealyticum*) as well as Mycobacteria, for example *Mycobacterium tuberculosis*. This list of microbes is purely illustrative and is in no way to be interpreted as restrictive.

In one embodiment, the disease or condition is or results from Methicillin-resistant *Staphylococcus aureus* (MRSA).

Examples of microbial infections or illness that can be treated by administration of the composition of the present invention include, but are not limited to, microbial infections or illnesses in humans such as, for example, otitis, pharyngitis, pneumonia, peritonitis, pyelonephritis, cystitis, endocarditis, systemic infections, bronchitis (acute and chronic), sepsis, illnesses of the upper airways, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmon, wound infections, infected burns, burns, infections in the mouth (including, e.g., but not limited to, periodontal disease and gingivitis), infections after dental operations, osteomyelitis, septic arthritis, cholecystitis, peritonitis with appendicitis, cholangitis, intraabdominal abscesses, pancreatitis, sinusitis, mastoiditis, mastitis, tonsileitis, typhoid, meningitis and infections of the nervous system, salpingitis, endometritis, genital infections, pelveoperitonitis and eye infections.

In one embodiment, the disease or condition is or results from a viral infection. Examples of viral infections that can be treated by administration of the peptoid oligomers of the present invention include, but are not limited to, viral infections caused by human immunodeficiency virus (HIV-1, HIV-2), hepatitis virus (e.g., hepatitis A, hepatitis B, hepatitis C, hepatitis D, and hepatitis E viruses), herpesviruses (e.g. herpes simplex virus types 1 and 2, varicella-zoster virus, cytomegalovirus, Epstein Barr virus, and human herpes viruses types 6, 7, and 8), influenza virus, respiratory syncytial virus (RSV), vaccinia virus, and adenoviruses. This list is purely illustrative and is in no way to be interpreted as restrictive.

It will be appreciated by skilled practitioners that subjects suffering from viral illnesses frequently succumb to secondary bacterial and/or fungal infections. Accordingly, in an embodiment of the invention pertaining to treating a disease or condition associated with a viral infection, an attending physician will be monitoring the patient for signs indicating the onset of such a secondary infection.

In one embodiment, the disease or condition is or results from a fungal infection. Examples of fungal infections or illnesses that can be treated by administration of the compositions of the present invention include, but are not limited to, fungal infections caused by Chytridiomycetes, Hyphochrytridiomycetes, Plasmodiophoromycetes, Oomycetes, Zygomycetes, Ascomycetes, and Basidiomycetes. Fungal infections which can be inhibited or treated with compositions of the peptoid oligomers provided herein include, but are not limited to: Candidiasis, including, but not limited to, onchomycosis, chronic mucocutaneous candidiasis, oral candidiasis, epiglottistis, esophagitis, gastrointestinal infections, genitourinary infections, for example, caused by any *Candida* species, including, but not limited to, *Candida albicans, Candida tropicalis, Candida* (*Torulopsis*) *glabrata, Candida parapsilosis, Candida lusitaneae, Candida rugosa* and *Candida pseudotropicalis*; Aspergillosis, including, but not limited to, granulocytopenia caused, for example, by, *Aspergillus* spp. Including, but not limited, to *Aspergillus fumigatus, Aspergillus favus, Aspergillus niger* and *Aspergillus terreus*; Zygomycosis, including, but not limited to, pulmonary, sinus and rhinocerebral infections caused by, for example, zygomycetes such as *Mucor, Rhizopus* spp., *Absidia, Rhizomucor, Cunningamella, Saksenaea, Basidobolus* and *Conidobolus*; Cryptococcosis, including, but not limited, to infections of the central nervous system, e.g., meningitis, and infections of the respiratory tract caused by, for example, *Cryptococcus neoformans*; Trichosporonosis caused by, for example, *Trichosporon beigelii*; Pseudallescheriasis caused by, for example, *Pseudallescheria boydii; Fusarium* infection caused by, for example, *Fusarium* such as *Fusarium solani, Fusarium moniliforme* and *Fusarium proliferartum*; and other infections such as those caused by, for example, *Penicillium* spp. (generalized subcutaneous abscesses), *Trichophyton* spp., for example, *Trichophyton mentagrophytes* and *Trichophyton rubrum, Stachybotrys* spp., for example, *S. chartarum, Drechslera, Bipolaris, Exserohilum* spp., *Paecilomyces lilacinum, Exophila jeanselmei* (cutaneous nodules), *Malassezia furfur* (folliculitis), *Alternaria* (cutaneous nodular lesions), *Aureobasidium pullulans* (splenic and disseminated infection), *Rhodotorula* spp. (disseminated infection), *Chaetomium* spp. (empyema), *Torulopsis candida* (fungemia), *Curvularia* spp. (nasopharnygeal infection), *Cunninghamella* spp. (pneumonia), *H. Capsulatum, B. dermatitidis, Coccidioides immitis, Sporothrix schenckii* and *Paracoccidioides brasiliensis, Geotrichum candidum* (disseminated infection). The compositions of the present invention can also be used to kill or inhibit the growth of any of the fungi listed above. This list is purely illustrative and is in no way to be interpreted as restrictive.

In one embodiment, the invention provides a method of using pharmaceutical composition of peptoid of formula Ia and/or Ib, to generation of antiseptic or sterile environment.

In one embodiment, the invention provides a method for preventing, treating, ameliorating or managing a disease or condition, which comprises administering to a patient in need of such prevention, treatment, amelioration or management a prophylactically or therapeutically acceptable amount of a peptoid of formula Ia and/or Ib, or the pharmaceutical composition thereof, wherein the disease or condition results from or is caused by bacterial infection, viral infection or fungal infection.

Pharmaceutical Compositions

When employed as pharmaceuticals, the peptoid compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the peptoid compounds in combination with one or more non-peptoid antibiotic compounds, including known antibiotic compounds. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the peptoid compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, rectal, vaginal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The present complexes may be used as therapeutic agents for the treatment of conditions in mammals. Accordingly, the complexes and pharmaceutical compositions of this invention find use as therapeutics for preventing and/or treating infections and like maladies resulting from bacterial, viral or fungal attack, and related conditions in mammals, including humans. Thus, and as stated earlier, the present invention includes within its scope, and extends to, the recited methods of treatment, as well as to the compounds for such methods, and to the use of such compounds for the preparation of medicaments useful for such methods.

In a method of treatment aspect, this invention provides a method of treating a mammal susceptible to or afflicted with a condition associated with or resulting from bacterial, viral or fungal attack or infection, which method comprises administering an effective amount of one or more of the pharmaceutical compositions just described.

The methods disclosed herein have veterinary applications and can be used to treat a wide variety of non-human vertebrates. Thus, in other aspects of the invention, the compositions of the present invention are administered in the above methods to non-human vertebrates, such as wild, domestic, or farm animals, including, but not limited to, cattle, sheep, goats, pigs, dogs, cats, and poultry such as chicken, turkeys, quail, pigeons, ornamental birds and the like.

The following are examples of microbial infections in non-human vertebrates that can be treated by administering a composition of the present invention: Pig: coli diarrhoea, enterotoxaemia, sepsis, dysentery, salmonellosis, metritis-mastitis-agalactiae syndrome, mastitis; ruminants (cattle, sheep, goat): diarrhoea, sepsis, bronchopneumonia, salmonellosis, pasteurellosis, mycoplasmosis, genital infections; horse: bronchopneumonias, joint ill, puerperal and post-puerperal infections, salmonellosis; dog and cat: bronchopneumonia, diarrhoea, dermatitis, otitis, urinary tract infections, prostatitis; poultry (chicken, turkey, quail, pigeon, ornamental birds and others): mycoplasmosis, *E. coli* infections, chronic respiratory tract illnesses, salmonellosis, pasteurellosis, psittacosis. This list is purely illustrative and is in no way to be interpreted as restrictive.

In additional method of treatment aspects, this invention provides methods of treating a mammal susceptible to or afflicted with a variety of bacteria or other infections, including strains which have developed resistance to traditional antibiotics, such as, for example, *Staphylococcus aureus*. The method comprises administering an effective condition-treating or condition-preventing amount of one or more of the pharmaceutical compositions just described.

The peptoid antimicrobials of the invention may also be used in preventive or prophylactic applications, wherein the peptoid antimicrobials are administered to a subject for preventive purposes (i.e., administered to a subject in advance of exposure to a disease causing entity) individually or as a combination of different peptoid antimicrobials. The peptoid antimicrobials of the invention can also be used in combination with antibiotics administered in a preventive application. A number of antibiotics are used clinically to reduce the risk of contracting bacterial, viral, and/or fungal infections. Ideally such preventive or prophylactic administration prevents infection.

In general, prophylactic administration of antibiotics is recommended only in certain situations or for people with particular medical problems. People with abnormal heart valves, for example, have a high risk of developing heart valve infections even after minor surgery. Such infections occur because bacteria from other parts of the body can enter the bloodstream during surgical procedures and travel to the heart valves. To prevent these infections, people with abnormal heart valves often take antibiotics before having any kind of surgery, including dental surgery.

Antibiotics may also be prescribed to prevent infections in people with weakened immune systems such as those with Acquired Immune Deficiency Syndrome (AIDS) or people who are having chemotherapy treatments for cancer. Even healthy people with strong immune systems, however, may occasionally be given preventive antibiotics if they are scheduled to have surgery that is associated with a high risk of infection, or if they are traveling to parts of the world where they are likely to contract an infection that causes, for example, diarrhea.

Drugs used for antibiotic prophylaxis include: amoxicillin (a type of penicillin) and fluoroquinolones such as ciprofloxacin (Cipro) and trovafloxacin (Trovan). These drugs are available in tablet, capsule, liquid, and injectable forms. Other antibiotics used for prophylactic purposes are known to those skilled in the art.

The following list presents particular embodiments wherein antibiotics are used for preventive purposes, wherein the peptoid antimicrobials of the invention may also be used to advantage either alone or in combination with prophylactic antibiotics. For malaria prophylaxis, clinicians prescribe 100 mg (e.g., doxycycline) by mouth daily 1-2 weeks prior to travel then 4 weeks after travel. For AIDS patients, *pneumocystis carinii* pneumonia prophylaxis is recommended and generally involves administration of Bactrim (trimethoprim-sulfamethoxazole), double strength tablet, one tablet by mouth daily. For AIDS patients, suppression of cryptococcal meningitis relapse is recommended and generally involves administration of fluconazole, 200 mg daily. Patients with other immunocompromising conditions (e.g., bone marrow transplant patients and neutropenic patients on chemotherapy) are also prescribed prophylactic oral antibiotics to prevent opportunistic infections by common fungal or bacterial agents.

For surgical prophylaxis, the cephalosporin antibiotics are usually preferred. This class includes cefazolin (Ancef, Kefzol), cefamandole (Mandol), cefotaxime (Claforan), and others. The choice of drug depends on its spectrum and the type of bacteria that are most likely to be encountered. Surgery on the intestines, for example, which are filled with many anaerobic bacteria, might call for cefoxitin (Mefoxin), while in heart surgery, where there are no anaerobes, cefazolin might be preferred.

The following list presents particular embodiments wherein antibiotics are used for surgical prophylaxis, wherein the peptoid antimicrobials of the invention may also be used to advantage either alone or in combination with prophylactic antibiotics. For patients with valvular heart disease, patients with a history of any valvular heart disease may be administered oral amoxicillin prior to dental work. Patients with a history of major valvular heart disease (like a valve replacement) may be administered iv antibiotics (usually ampicillin, 1 gram every 6 hours and gentamicin 80 mg every 8 hours) prior to, during and after major abdominal surgery.

As pre-operative antibiotics, any patient having abdominal surgery may be treated with antibiotics intravenously (iv). Typically, patients receive one dose of a cephalosporin (Cefotetan, Cefoxitin, etc.), about 1 gram iv. For heavy intra-operative bleeding or operations lasting longer than 4 hours, another dose of iv antibiotics may be given and, in extended use, iv antibiotics may be administration for 24 hours after the operation. For bowel surgery, general surgeons will frequently administer iv Ciprofloxacin 400 mg and Metronidazole 500 mg. In cases of emergency surgery, post-operative antibiotics are usually given to prevent infection. In all cases, the antibiotic administered is determined by the attending medical practitioner, based on experience as to which microbial agents the patient is most likely to be exposed.

A skilled practitioner would appreciate applications wherein the peptoid antimicrobials of the invention may be used to advantage, alone or in conjunction with antibiotics for prophylactic purposes. In a particular embodiment, peptoid antimicrobials of the invention may be administered alone or in conjunction with antibiotics for preventing bacterial infections.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as those associated with persistent viral or microbial conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

The complexes of this invention can be administered as the sole active agent or they can be administered in combination with other agents, including other active derivatives.

A skilled practitioner would appreciate that the choice as to which compound or compounds of the invention are well suited to a particular application must take into consideration such variables as the severity of the disease or condition, mode of administration, duration of administration, and the cost:benefit ratio associated with synthesis of linear versus cyclic peptoids.

Antimicrobial Substrates

The peptoid oligomers of the present invention and compositions thereof may also be bound to or incorporated into substrates to provide antimicrobial substrates to reduce or inhibit microbial contamination of the substrate. The present invention also provides articles comprising the antimicrobial substrates of the invention.

As indicated above, a skilled practitioner would take into consideration such variables as the likelihood of microbial contamination of a substrate prior to or during use, risks associated with microbial contamination in a subject using a substrate, duration of use, and the cost:benefit ratio associated with synthesis of linear versus cyclic peptoids.

Substrates suitable for the present invention include conventional polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures or blends thereof. Additional polymer substrates are also functionalized polymer substrates comprising the aforementioned polymers, which may further comprise or may be functionalized to comprise active groups with which peptoid oligomers may react, and which allow for immobilization of same. Examples of active groups include, but are not limited to: acrylic acid, acetal, hydroxyl, amines, epoxides, carboxylates, anhydrides, isocyanates, thioisocyanates, azides, aldehydes, halides, acyl halides, aryl halides and ketones at 1 to 50% by weight of the polymer. Various methods of protein or peptide immobilization are described in Protein Immobilization (Richard F. Taylor (ed.), Marcel Dekker, New York, 1991); similar methods may be used such as those familiar to practitioners skilled in the art of immobilization of peptoids.

Substrates suitable for the present invention also include ceramics, glass, metal, metal oxides, and composites comprised of ceramics, glass, metal or metal oxides plus polymers as described above. Suitable metals include steel, stainless steel, aluminum, copper, titanium, alloys thereof, and combinations thereof.

The articles of the present invention have antimicrobial peptoid oligomers of the invention bound to or incorporated into a substrate. The use of antimicrobial peptoid oligomers to confer antimicrobial properties to substrates provides many advantages due to the fact that the peptoid oligomers of the invention exhibit rapid biocidal activity, broad spectrum activity, and a reduced likelihood of resistance in target organisms compared to more traditional antimicrobials, such as antibiotics. Peptoid oligomers can be bound to a substrate either physicochemically, or covalently. Physicochemical binding of peptoid oligomers to the substrate may occur by any one or combinations of the following forces: electrostatic, hydrogen bonding, and Van der Waals. Alternatively, peptoid oligomers may be bound to the substrate surface by a covalent bond. Additionally, antimicrobial peptoid oligomers of the present invention can be incorporated into the polymer by mixing with the polymer, for example by dissolving the peptoid oligomer and the polymer in a common solvent and casting or molding the peptoid oligomer:polymer mixture into an article.

In one embodiment, the antimicrobial peptoid oligomer is bound to the substrate by coating a substrate polymer with an aqueous or non-aqueous solution of the peptoid oligomer, wherein the peptoid oligomer is at concentration ranging from about 0.0001 to about 20 weight percent. The peptoid oligomer is contacted with the substrate polymer, and the peptoid oligomer and substrate polymer are optionally shaken at temperatures ranging from about −10° C. to about 150° C. for a period of time ranging from about 0.1 min to about 96 hrs. Preferably the peptoid oligomer and substrate polymer are shaken at a temperature of from about 25° C. to about 80° C. for a period of time ranging from about 1 min to about 24 hrs.

In another embodiment, the substrate polymer is primed to generate active groups that will bind to the antimicrobial peptoid oligomer. Surface modification of the polymer may be achieved by a variety of techniques well known in the art including: oxidation, reduction, hydrolysis, plasma, and irradiation. Substrate polymers containing acid or base hydrolyzable groups such as polyesters, polyamides, and polyurethanes may be treated with acid or base first. Subsequently, the hydrolyzed polymer is brought into contact with an aqueous or non-aqueous solution of from about 0.001 to about 20 weight percent of the antimicrobial peptoid oligomer. The peptoid oligomer and the polymer may be shaken at temperatures ranging from about −10° C. to about 150° C. for a period of time ranging from about 0.1 min to about 96 hrs. Preferably the peptoid oligomer and substrate polymer are shaken at a temperature of from about 25° C. to about 80° C. for a period of time ranging from about 10 min to about 24 hrs.

In another embodiment, a commercial substrate polymer containing 1-50% active groups is brought into contact with an aqueous or non-aqueous solution comprising from about 0.0001 to about 20 weight percent of the antimicrobial peptoid oligomer.

Methods for binding or incorporating peptides and/or peptoids to substrates are known to those of skill in the art who would, moreover, be aware of additional modifications to the above general guidelines that could be implemented, as required, to improve binding or incorporation of the peptoid oligomers of the invention to substrates. U.S. Pat. No. 7,307,061, for example, describes such methods in detail and is incorporated herein in its entirety.

After treatment with the antimicrobial peptoid oligomer, the article may be washed, preferably with deionized water. Optionally, the article may then be dried via methods known in the art. Such methods include ambient air drying, oven drying, and air forced drying. In one preferred embodiment, the article is dried at about 50° C. to about 120° C., more preferably at about 50° C. to about 100° C., for about 15 min to about 24 hrs.

Articles comprising the polymer substrate of the present invention may be in the form of or comprise an extrudate, film, membrane, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of substrates are included in the present invention. The following are examples of articles wherein it is desirable to reduce microbial growth in or on the article in the end-use for which the particular article is commonly used.

The articles of the invention include packaging for food, personal care (health and hygiene) items, and cosmetics. By "packaging" is meant either an entire package or a component of a package. Examples of packaging components include but are not limited to packaging film, liners, absorbent pads for meat packaging, tray/container assemblies, caps, adhesives, lids, and applicators. The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging, and caps.

Examples of applicators include those for lipstick, chapstick, and gloss; packages and applicators for eye cosmetics, such as mascara, eyeliner, shadow, dusting powder, bath powder, blusher, foundation and creams. These applicators are used to apply substances onto the various surfaces of the body and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is to be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; and machines for food cutting and slicing and components thereof. Where the surface of such equipment components is metal, the metal could be coated directly, or a coating of a polymer or functionalized polymer could first be applied to the metal surface. Alternatively, a film of such a polymer or functionalized polymer could be coated with an antimicrobial peptoid oligomer of the invention and then applied to the equipment surface. Additional articles of the invention include foods and seeds.

Articles of the present invention can also be used in or as items of apparel, such as a swimsuit, undergarment, shoe component (for example, a woven or nonwoven shoe liner or insert), protective sports pad, or child's garment. Articles of the invention also include protective medical garments or barrier materials, such as gowns, masks, gloves, slippers, booties, head coverings or drapes.

Articles of the present invention can also be used in or as medical materials, devices, or implants, such as bandages, adhesives, gauze strips, gauze pads, syringe holders, catheters such as peripheral IV catheters and central venus catheters comprised of either polyurethane or silicon, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

In the hygiene area, articles of the present invention include personal hygiene garments such as diapers, incontinence pads, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy. Additional child-oriented articles that benefit from the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of separation membranes (for example, pervaporation, dialysis, reverse osmosis, ultrafiltration, and microfiltration membranes) comprised of polymer substrates of the invention.

As used herein and referred to in the art, a biofilm is an aggregate of microbes with a distinct architecture. A biofilm is essentially a collective in which microbial cells, each only a micrometer or two long, form towers that can be hundreds of micrometers high. The channels between the towers act as fluid-filled conduits that circulate nutrients, oxygen, waste products, etc., as required to maintain a viable biofilm community. The biofilm or microbial (bacterial, fungal, or algal) community is typically enveloped by extracellular biopolymers produced by the microbial cells and adheres to the interface between a liquid and surface. The encapsulated property of biofilms renders the microbial organisms therein highly resistant to standard anti-microbial therapeutics. Bacteria growing in a biofilm, for example, are highly resistant to antibiotics, and in some cases are up to 1,000 times more resistant than the same bacteria growing without a biofilm superstructure. Standard antibiotic therapy can be useless wherein a biofilm contaminated implant is detected and the only recourse under such circumstances may be to remove the contaminated implant. Fungal biofilms also frequently contaminate medical devices. They can cause chronic vaginal infections and lead to life-threatening systemic infections in immunocompromised individuals. Biofilms are, furthermore, involved in numerous diseases. Cystic fibrosis patients, for example, suffer from *Pseudomonas* infections that often result in antibiotic resistant biofilms.

The antimicrobial peptoid oligomers of the invention are well suited to applications directed to the prevention of biofilm formation or eradication of a pre-existing biofilms because they act quickly, exhibit good permeability, and are resistant to proteolysis. As indicated herein above, these advantageous properties also apply to other uses of the antimicrobial peptoid oligomers of the invention.

In order to impart antimicrobial functionality to the products listed, the product can be treated with an antimicrobial peptoid oligomer of the invention before it is manufactured, or after, or at any time during manufacture of the product. For example, in making an antimicrobial shower curtain, an antimicrobial peptoid oligomer of the invention may be bound to or incorporated into the polymer substrate, followed by fashioning a shower curtain from the treated material. Alternatively, treatment of the polymer substrate with an antimicrobial peptoid oligomer of the invention may be performed after the substrate is made into a shower curtain.

Antimicrobial substrates or articles prepared by methods of the invention exhibit antimicrobial functionality, wherein microbes are killed, or microbial growth is reduced or prevented. Antimicrobial activity of the antimicrobial substrate or article can be determined by using any of a number of methods well known in the art, such as the Shake Flask Test described in U.S. Pat. No. 7,307,061 and United States Patent Application No. 2008/0081789, the entire contents of which are incorporated herein in their entireties. Additional methods for determining antimicrobial activity are discussed in Tenover et al. (eds.), Manual of Clinical Microbiology, 7.sup.th Edition, Section VIII, 1999, American Society for Microbiology, Washington, D.C.

Additional Assays for Evaluation of Antibacterial Efficacy

In Vivo Thigh Burden Infection Model.

The evaluation of compounds in the mouse thigh burden infection model may be performed as follows. A skilled practitioner would be aware of modifications to the protocol as set forth below and would further appreciate that the protocol may be modified in accordance with accepted practice. Female CD-1 mice may be used that are 6- to 8-weeks-old and weigh within the range of 20 to 26 g. Mice are rendered neutropenic with 2 intraperitoneal (i.p.) injections of cyclophosphamide (150 mg/kg in 10 mL/kg) at 4 and 1 days before inoculation. Inoculum for studies may be prepared by transferring colonies from 18-20-h tryptic soy agar (TSA) cultures to sterile PBS and adjusting the density to approximately $10^6$ CFU/mL using a spectrophotometer. The inoculum concentration may be determined using the dilution plate count method. Mice are inoculated by injecting each posterior thigh with 0.1 mL of inoculum. After treatment with compound at each time point, thighs are harvested at 25 h after inoculation. Quantification of bacteria is conducted by aseptically removing the thighs (muscle and bone) and placing them in a sterile tared tube. The tube is weighed and 5 mL of sterile PBS added. The contents are homogenized with a tissue homogenizer (Polytron Model 3100) for approximately 20 sec. Aliquots (0.1 mL) of serial dilutions are plated on TSA. Plates are incubated at 37° C. for 20 h. Colony counts are used to calculate CFU per thigh.

General Synthetic Procedures

The complexes of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative peptoid oligomers that have been listed hereinabove. The peptoid oligomers of the invention may be prepared from known or commercially available starting materials and reagents by one skilled in the art of organic synthesis.

Solvents and reagents purchased from commercial sources were used without further purification. Abbreviations for reagents are as follows: 9-fluorenylmethoxycarbonyl (Fmoc); tert-butoxycarbonyl (Boc); benzotriazole-1-yl-oxy-tris-pyrrolidino-phosphonium hexafluorophosphate (PyBOP); Bromo-tris-pyrrolidino phosphoniumhexafluorophosphate (PyBrOP); trifluoroacetic acid (TFA); hexafluoroisopropyl alcohol (HFIP); methylene chloride (DCM); N,N'-dimethylformamide (DMF); N,N'-diisopropylcarbodiimide (DIC); diisopropylethylamine (DIEA); acetonitrile (ACN); N-methylmorpholine (NMM); 0-Benzotriazole-N,N,N',N'-tetramethyl-uronium-hexafluoro-phosphate (HBTU).

Representative Synthetic Method

Preparation of Peptoid Oligomers of the Invention

General protocols for the synthesis of both linear and cyclic peptoid oligomers are shown in Scheme 1. These sequence-specific N-substituted glycine oligomers can be efficiently synthesized via "submonomer chemistry" methods to incorporate a large number of diverse side chain chemical functionalities (Figliozzi et al, Synthesis of N-substituted glycine peptoid libraries. In *Methods Enzymol.*, Academic Press: 1996; Vol. 267, pp 437-447; Bartlett et al., *Proc. Natl. Acad. Sci. U.S.A.* 1992, 89, 9367-9371). This approach iterates sequential steps of bromoacylation and nucleophilic displacement to construct each monomer unit. The side chain moieties are introduced upon the displacement of bromide by diverse primary amine submonomer reagents.

Scheme 1: Synthesis (A) N-acetylated linear peptoid oligomers and (B) cyclic peptoid oligomers.

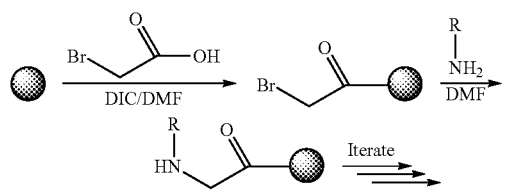

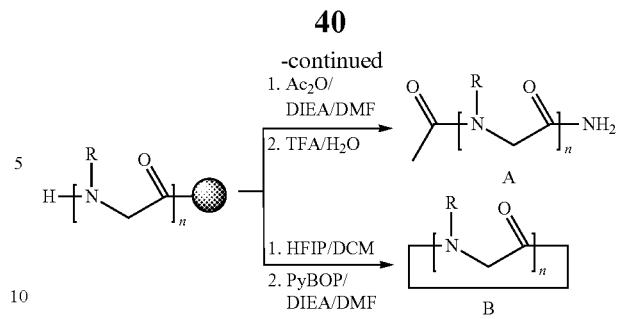

wherein R = R$^1$, and R$^1$ is as described herein.
DIC: diisopropylcarbodiimide; DMF: N, N-dimethylformamide; DIEA: diisopropylethylamine; TFA: trifluoroacetic acid; HFIP: 1,1,1,3,3,3-hexafluoroisopropanol. *Rink Amide resin was used to generate N-acetylated linear oligomers and 2-chlorotrityl chloride resin was used to generate cyclic peptoid oligomers. ** n = 6, 8, 10

N-acetylated linear oligomers were synthesized on Rink® Amide resin to afford peptoid C-terminal amides. The N-terminus was acetylated with acetic anhydride prior to TFA cleavage. Macrocyclic peptoid oligomers were generated from linear precursors containing free N-terminal amino groups and C-terminal carboxylic acid groups in PyBOP/DIEA/DMF. The linear precursors were synthesized on 2-chlorotrityl resin and cleaved with 20% HFIP/DCM.

Synthesis and Purification of Cyclic Peptoid Oligomers

Previously reported solid phase peptoid synthesis protocols were used with adjustments in reaction time and washing conditions. Peptoid synthesis was performed using an automated synthesizer (Charybdis Technologies Inc., San Diego, Calif.) at room temperature. Peptoid oligomers were synthesized on 2-chlorotrityl chloride resin (NovaBiochem; 100-200 mesh; 1.1 mmol/g).

For the generation of N-(3-aminopropyl)glycine (Nap), N-(4-aminobutyl)glycine (Nab), N-(6-aminohexyl)glycine (Nah), and N-(4-guanidinobutyl)glycine (Ngb) residues, N-Boc-1,3-diaminopropane, N-Boc-1,4-diaminobutane, N-Boc-1,6-diaminohexane, and N,N'-bis-Boc-agmatine were used as the submonomer reagents, respectively.

N-Boc-1,3-diaminopropane, N-Boc-1,4-diaminobutane, and N-Boc-1,6-diaminohexane were synthesized from di-tert-butyl dicarbonate (Alfa Aesar) and corresponding diaminoalkanes (1,3-diaminopropane (Sigma-Aldrich), 1,4-diaminobutane (Alfa Aesar), and 1,6-diaminohexane (Acros)) following the previously reported protocol (Dardonville et al. *Bioorg. Med. Chem.* 2006, 14, 6570-6580).

N,N'-bis-Boc-agmatine was synthesized from 1,4-diaminobutane (Alfa Aesar) and N,N'-bis-Boc-methylisothiourea (Sigma-Aldrich) following the previously reported protocol (Sarabia et al. *Bioorg. Med. Chem.* 2005, 13, 1691-1705).

For the generation of N-(phenylmethyl)glycine (Npm), N-(naphthylmethyl)glycine (Nnm), N-(2,2-diphenylethyl) glycine (Ndp), N-isopropylglycine (Nip), and N-isobutylglycine (Nib) residues, benzylamine (Alfa Aesar), napthylmethylamine (Sigma-Aldrich), 2,2-diphenylethylamine (Acros), isopropylamine (Alfa Aesar), and isobutyl amine (Sigma-Aldrich) were used as the submonomer reagents respectively.

Typically, for the generation of cyclic peptoid oligomers, 200 mg of 2-chlorotrityl chloride resin was washed twice in 2 mL of DCM, followed by swelling in 2 mL of DCM. The first monomer was added manually by reacting 37 mg of bromoacetic acid (0.27 mmol; Sigma-Aldrich) and 189 µL of DIEA (1.08 mmol; Chem Impex International) in 2 mL of DCM on a shaker platform for 30 minutes at room temperature, followed by extensive washes with DCM (five times with 2 mL) and DMF (five times with 2 mL). Bromoacylated resin was incubated with 2 mL of 1 M amine submonomer in DMF on a shaker platform for 30 minutes at room temperature, followed by extensive washes with DMF (five times with 2 mL). After initial manual loading of bromoacetic acid, the first submonomer displacement step and all subsequent bromoacetylation and amine displacement steps were performed by a robotic synthesizer until the desired oligomer length was obtained. The automated bromoacetylation step was performed by adding 1660 µL of 1.2 M bromoacetic acid in DMF and 400 µL of DIC (Chem Impex International). The mixture was agitated for 20 min, drained, and washed with DMF (three times with 2 mL). Next, 2 mL of a 1 M solution of submonomer (2 mmol) in DMF was added to introduce the side chain by nucleophilic displacement of bromide. The mixture was agitated for 20 min, drained, washed with DMF (three times with 2 mL) and washed with DCM (three times with 2 mL). The peptoid-resin was cleaved in 2 mL of 20% HFIP (Alfa Aesar) in DCM (v/v) at room temperature. The cleavage was conducted in a glass tube with constant agitation for 30 minutes. HFIP/DCM was evaporated under a stream of nitrogen gas. The final product was dissolved in 5 mL of 50% ACN in HPLC grade $H_2O$ and filtered with a 0.5 µm stainless steel fitted syringe tip filter (Upchurch Scientific). Peptoid oligomers were analyzed on a $C_{18}$ reversed-phase analytical RP-HPLC column at room temperature (Peeke Scientific, 5 µm, 120 Å, 2.0×50 mm) using a Beckman Coulter System Gold instrument. A linear gradient of 5-95% acetonitrile/water (0.1% TFA, Acros Organics) over 20 min was used with a flow rate of 0.7 mL/min. In order to remove any traces of HFIP in the sample solution, linear precursors dissolved in 50% ACN/$H_2O$ were freeze-dried overnight.

Cyclization reactions were conducted, with crude linear precursors, in dry, deoxygenated DMF. 12 µmoles of the purified linear oligomer was suspended in 5.25 mL of DMF in a 15 mL conical tube. 375 µL of PyBOP (NovaBiochem) solution (96 mM, freshly prepared in DMF) and 375 µL of DIEA solution (192 mM, freshly prepared in DMF) were added to the peptoid. The reaction vessel was flushed with nitrogen and sealed to exclude air. The reaction proceeded for 5 minutes at room temperature and 10 µL of reaction mixture was diluted with 140 µL of 50% ACN in $H_2O$ to quench the reaction. The diluted sample was analyzed by HPLC. Preparative HPLC was performed on a Delta-Pak $C_{18}$ (Waters, 15 µm, 100 Å, 25×100 mm) with a linear gradient of 5-95% acetonitrile/water (0.1% TFA) over 60 min with a flow rate of 5 mL/min. LC-MS was performed on an Agilent 1100 Series LC/MSD Trap XCT (Agilent Technologies). Purified HPLC fraction was freeze-dried. Boc protecting groups were removed with 5 mL of 95% TFA/$H_2O$ over 30 minutes at room temperature. Stream of nitrogen gas was used to reduce the volume of TFA solution down to 10% of its original volume. Concentrated sample was dissolved in 15 mL of 50% ACN/$H_2O$ and freeze-dried.

Synthesis and Purification of Gramicidin S

Peptide gramicidin S sequence was synthesized using standard Fmoc solid-phase peptide synthesis protocols. 200 mg of 2-chlorotrityl chloride resin (NovaBiochem; 100-200 mesh; 1.1 mmol/g) was washed twice in 2 mL of DCM, followed by swelling in 2 mL of DCM. The first amino acid was added manually by reacting 0.27 mmol of Fmoc-Phe (NovaBiochem) and 142 µL of DIEA in 2 mL of DCM on a shaker platform for 30 minutes at room temperature, followed by extensive washes with DCM (five times with 2 mL) and DMF (five times with 2 mL). Resin loaded with Fmoc-Phe was incubated twice with 2 mL of 20% piperidine/DMF (v/v) on a shaker platform for 15 minutes at room temperature, followed by extensive washes with DMF (five times with 2 mL). After manual loading of Phe, all subsequent amino acid addition and Fmoc deprotection steps were performed on a robotic synthesizer (Charybdis Technologies Inc., San Diego, Calif.) until the desired peptide length was obtained. Fmoc-Phe-OH, Fmoc-Leu-OH, Fmoc-Orn(Boc)-OH, Fmoc-Val-OH, and Fmoc-Pro-OH were purchased from NovaBiochem (San Diego, Calif.). The automated amino acid addition step was performed by adding 1 mL of 0.5 M Fmoc-amino acid in DMF, 1 mL of 0.5 M HBTU (NovaBiochem) in DMF and 1 mL of 1.5 M NMM (Alfa Aesar) in DMF. The mixture was agitated for 30 min, drained, and washed with DMF (three times with 2 mL). Next, the resin was incubated twice with 2 mL of a 20% piperidine/DMF (v/v) for 15 minutes. The reaction was drained and washed with DMF (three times with 2 mL) and washed with DCM (three times with 2 mL). The peptide-resin was cleaved in 2 mL of 20% HFIP in DCM (v/v) at room temperature. The cleavage was conducted in a glass tube with constant agitation for 30 minutes. HFIP/DCM was evaporated under a stream of nitrogen gas. The final product was dissolved in 5 mL of 70% ACN in HPLC grade $H_2O$. Peptide oligomers were analyzed by RP-HPLC and ESI mass spectrometry as described above. Cyclization of gramicidin S sequence was performed as described above.

N-Acetylated Linear Peptoid/Peptide Synthesis and Purification

Peptoid synthesis was performed using an automated synthesizer (Charybdis Technologies Inc., San Diego, Calif.) at room temperature. Peptoid oligomers were synthesized on 100 mg of Rink amide resin (NovaBiochem; 0.49 mmol/g). Rink amide resin (100 mg) was washed twice in 1.5 mL of DCM, followed by swelling in 1.5 mL of DMF. The swelling step was performed twice. The Fmoc protecting group was removed from the resin by addition of 20% piperidine/DMF. The mixture was agitated for 10 minutes, drained and the piperidine treatment was repeated, followed by extensive washes with DMF (five times with 1.5 mL). After removal of the Fmoc group, standard Fmoc solid-phase peptide synthesis protocols were used for the generation of linear peptide sequence, as described above.

After removal of the Fmoc group from the Rink amide resin, linear peptoid sequences were generated using the procedure performed by a robotic synthesizer and repeated until the desired oligomer length was obtained.

The amino-functionalized resin was bromoacetylated by adding 830 µL of 1.2 M bromoacetic acid (Sigma) in DMF and 200 µL of DIC (ChemImpex International). The mixture was agitated for 20 min, drained, and washed with DMF (three times with 1.5 mL). Next, 1 mL (1 mmole) of a 1 M solution of submonomer reagent in DMF was added to introduce the side chain by nucleophilic displacement of bromide. The mixture was agitated for 20 min, drained, washed with DMF (three times with 1.5 mL) and washed with DCM (three times with 1.5 mL).

After the last coupling step, the acetylated N-termini were generated using 1.5 mL of 1 M acetic anhydride/DMF and 50 µL of DIEA. The mixture was agitated for 20 min, drained, washed with DMF (three times with 1.5 mL) and washed with DCM (three times with 1.5 mL). N-terminal capped peptoid oligomers were cleaved in 3 mL of 95% TFA in HPLC grade H$_2$O (v/v) at 25° C. The cleavage was conducted in a glass vial with constant agitation for 120 minutes. The TFA/H$_2$O was removed under a stream of nitrogen gas. The final product was dissolved in 5 mL of 50% acetonitrile in HPLC grade H$_2$O and filtered with a 0.5 µm stainless steel fritted syringe tip filter (Upchurch Scientific). Peptoid/peptide oligomers were analyzed by RP-HPLC and ESI mass spectrometry as described above.

FIG. 1 shows a representative cyclization reaction monitored by RP-HPLC. The Boc protecting groups used on amino groups and guanidine groups were removed after the cyclization step in 95% TFA/H$_2$O.

Table 1 shows LC-MS data of all 32 compounds, following the removal of Boc protecting groups.

TABLE 1

ESI mass spectrometric data of compounds

| # | Compounds | Chemical Structure | Calculated Mass$^a$ | Observed Mass |
|---|---|---|---|---|
| 1 | Ac(Gramicidin S) | [structure] | 1199.74 | 1200.4 |
| 2 | Ac(NgbNpm)$_3$ | [structure] | 1010.59 | 506.2 (m + 2/2) |
| 3 | Ac(NahNpm)$_3$ | [structure] | 968.62 | 969.6 |
| 4 | Ac(NapNdp)$_3$ | [structure] | 1112.62 | 1113.6 |

TABLE 1-continued

ESI mass spectrometric data of compounds

| # | Compounds | Chemical Structure | Calculated Mass[a] | Observed Mass |
|---|-----------|--------------------|--------------------|----------------|
| 5 | Ac(NapNnm)$_3$ | 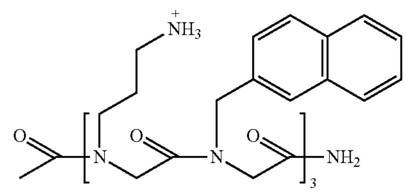 | 992.53 | 497.2 (m + 2/2) |
| 6 | Ac(NapNpm)$_2$Nap$_2$ | 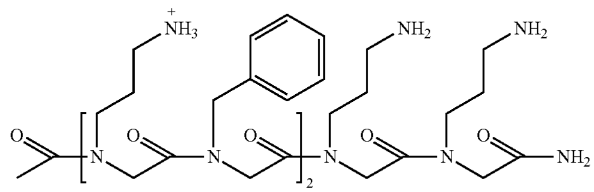 | 809.49 | 810.5 |
| 7 | Ac(NapNpm)$_3$ | 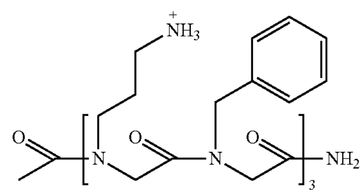 | 842.48 | 843.4 |
| 8 | Ac(NapNpm)$_4$ | 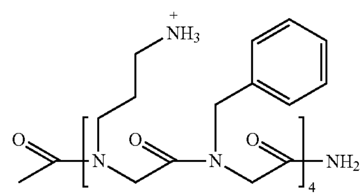 | 1103.63 | 1104.7 |
| 9 | Ac(NapNpm)$_5$ | 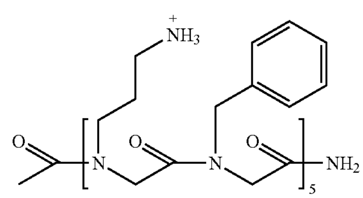 | 1364.78 | 1365.9 |
| 10 | Ac(NpmNap)$_2$Npm$_2$ | 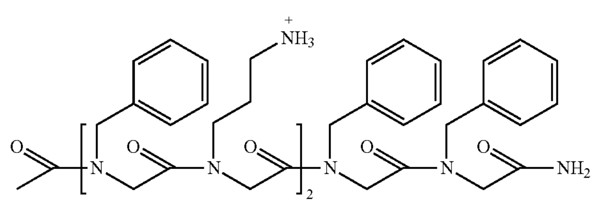 | 875.47 | 876.4 |

TABLE 1-continued

ESI mass spectrometric data of compounds

| # | Compounds | Chemical Structure | Calculated Mass[a] | Observed Mass |
|---|---|---|---|---|
| 11 | Ac(NipNapNibNpmPro)$_2$ | 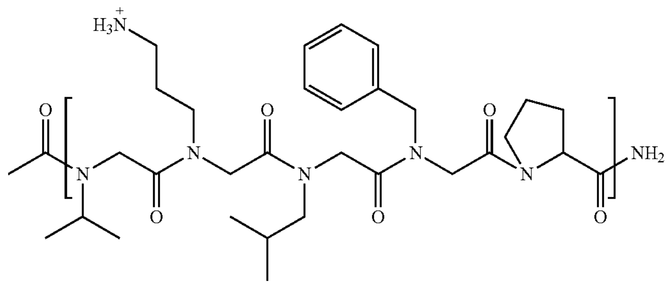 | 1199.74 | 1200.4 |
| 12 | Ac(NdpNibNgbNipPro)$_2$ | 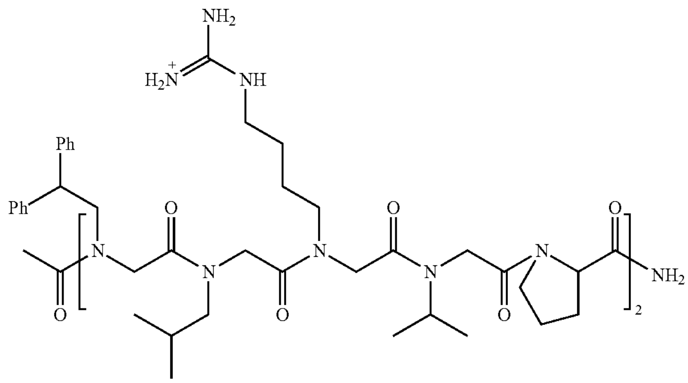 | 1491.91 | 746.7 (m + 2/2) |
| 13 | Ac(NpmNibNapNipPro)$_2$ | 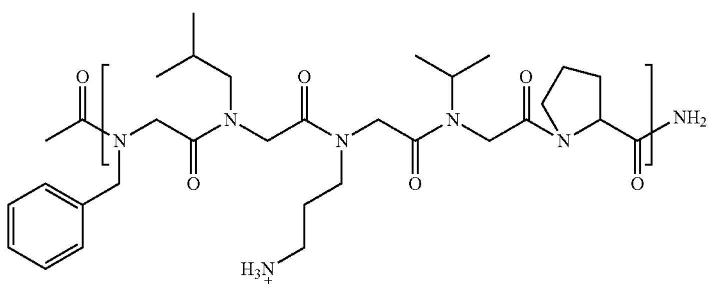 | 1199.74 | 1200.4 |
| 14 | Ac(NabNpm)$_3$ | 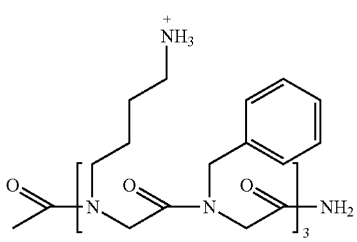 | 884.53 | 885.5 |
| 15 | Ac(NgbNdp)$_5$ | 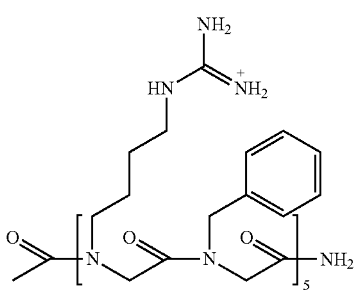 | 2095.2 | 699.5 (m + 3/3) |

TABLE 1-continued

ESI mass spectrometric data of compounds

| # | Compounds | Chemical Structure | Calculated Mass[a] | Observed Mass |
|---|---|---|---|---|
| 16 | Ac(NdpNgb)$_2$Ndp$_2$ | 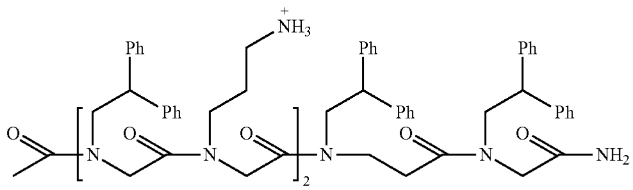 | 1347.73 | 1348.3 |
| 17 | C(Gramicidin S) | 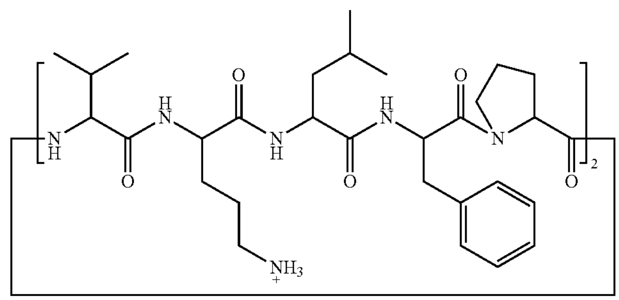 | 1140.71 | 1141.7 |
| 18 | C(NgbNpm)$_3$ | 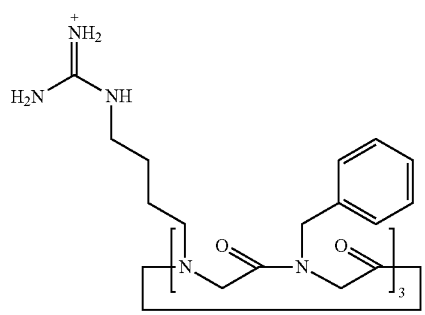 | 951.56 | 952.3 |
| 19 | C(NahNpm)$_3$ | 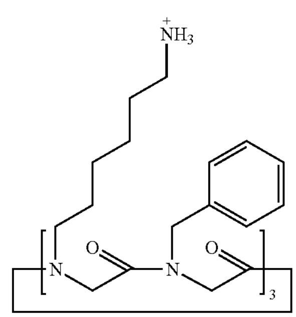 | 909.58 | 910.3 |
| 20 | C(NapNdp)$_3$ | 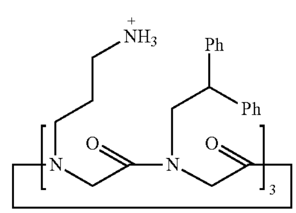 | 1053.58 | 1054.6 |

TABLE 1-continued
ESI mass spectrometric data of compounds
| # | Compounds | Chemical Structure | Calculated Mass[a] | Observed Mass |
|---|---|---|---|---|
| 21 | C(NapNnm)$_3$ | 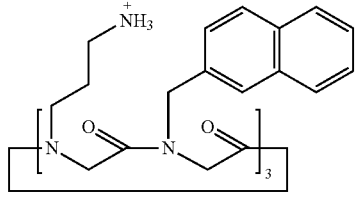 | 933.49 | 934.2 |
| 22 | C(NapNpm)$_2$Nap$_2$ | 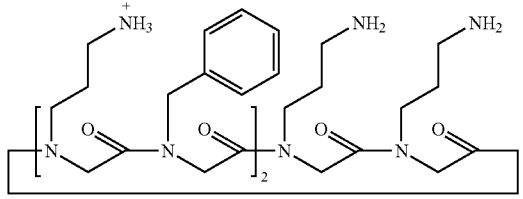 | 750.45 | 751.2 |
| 23 | C(NapNpm)$_3$ | 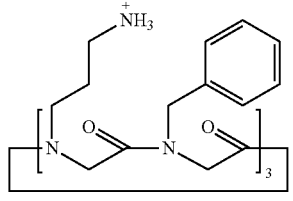 | 783.44 | 784.2 |
| 24 | C(NapNpm)$_4$ | 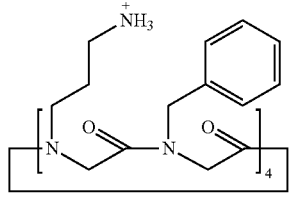 | 1044.59 | 1067.2 (m + Na) |
| 25 | C(NapNpm)$_5$ | 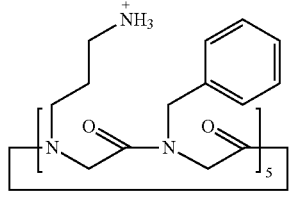 | 1305.74 | 1328.2 (m + Na) |
| 26 | C(NpmNap)$_2$Npm$_2$ | 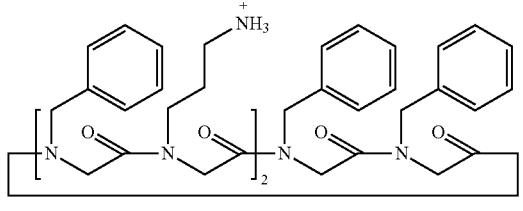 | 816.43 | 817.4 |

TABLE 1-continued

ESI mass spectrometric data of compounds

| # | Compounds | Chemical Structure | Calculated Mass[a] | Observed Mass |
|---|---|---|---|---|
| 27 | C(NipNapNibNpmPro)$_2$ | 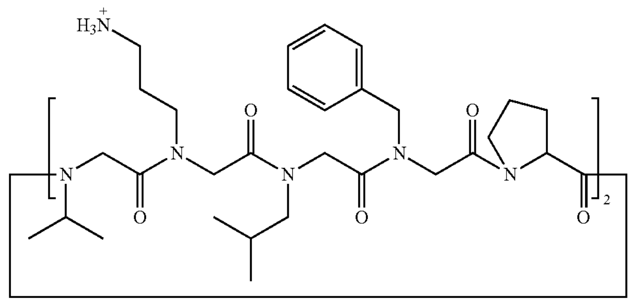 | 1140.71 | 1141.9 |
| 28 | C(NdpNibNgbNipPro)$_2$ | 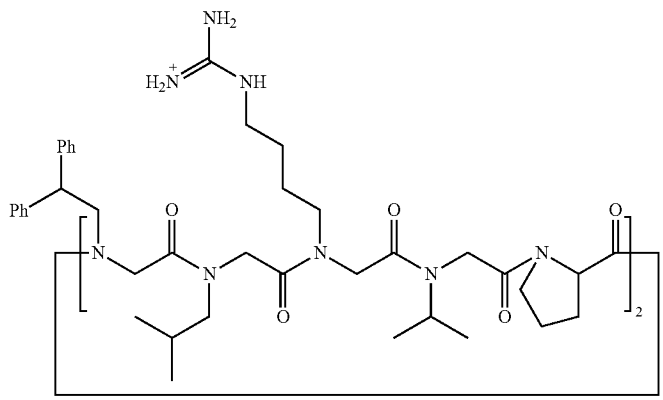 | 1432.87 | 717.3 (m + 2/2) |
| 29 | C(NpmNibNapNipPro)$_2$ | 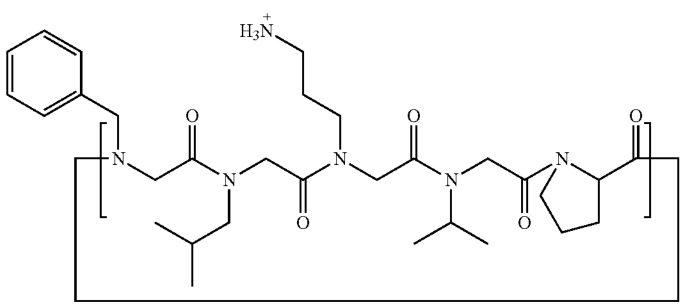 | 1140.71 | 1141.9 |
| 30 | C(NabNpm)$_3$ | 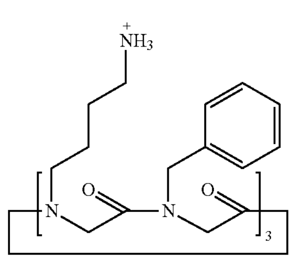 | 825.49 | 826.6 |

TABLE 1-continued

ESI mass spectrometric data of compounds

| # | Compounds | Chemical Structure | Calculated Mass[a] | Observed Mass |
|---|---|---|---|---|
| 31 | C(NgbNdp)$_5$ | (structure) | 2036.16 | 510.1 (m + 4)/4 |
| 32 | C(NdpNgb)$_2$Ndp$_2$ | (structure) | 1288.69 | 645.5 (m + 2/2) |

Side chain abbreviations are as described herein;
[a]Calculated mass = (m + H)/z;
Highlighted in bold type are peptide sequences;
Ac: acetylated; C: cyclic.

EXAMPLES

The following examples are presented in order to more fully illustrate the preferred embodiments of the invention. They should in no way be construed, however, as limiting the broad scope of the invention.

Example 1

Antimicrobial and Hemolytic Activity

Figure 2:
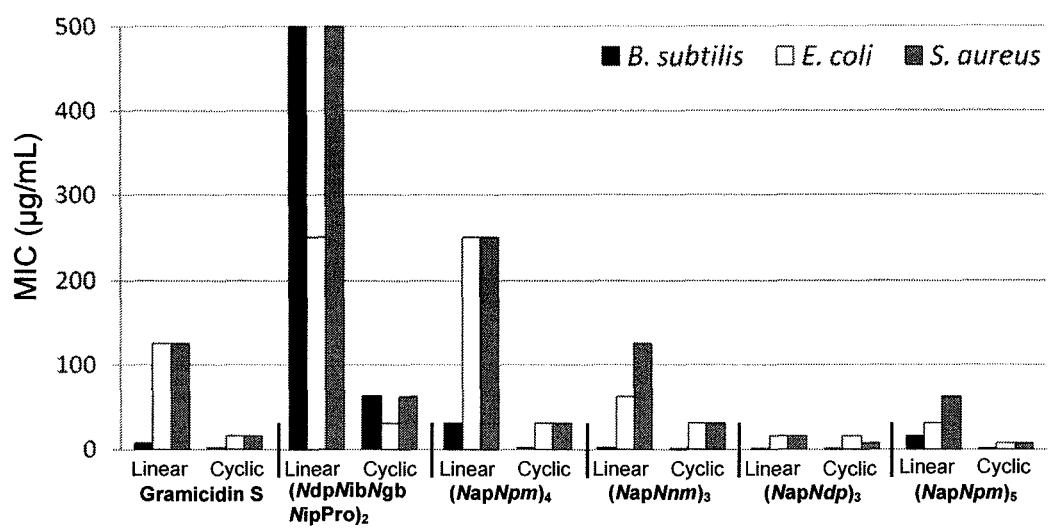
FIG. 2 shows antimicrobial activity data for 6 pairs of N-acetylated linear and cyclic compounds tested. MIC (Minimum Inhibitory Concentration) measures the lowest concentration of antimicrobial agent where microbes do not proliferate.

The most potent antimicrobial activities were detected from cyclic (NapNpm)$_5$, which showed minimum inhibitory concentrations (MIC) of 0.5 µg/mL for *B. subtilis*, 7.8 µg/mL for *E. coli*, and 7.8 µg/mL for *S. aureus*. Antimicrobial activity data for the six most potent N-acetylated linear and cyclic pairs of oligomers are shown in FIG. 2. Antimicrobial and hemolytic activity data for all 32 compounds in this study are shown in Table 2.

Peptoid sequences, both linear and cyclic, do not induce hemolysis of fresh human erythrocytes. Typically, toxicity is evaluated by hemolytic concentration$_{50}$ (HC$_{50}$), which measures the concentration of antimicrobial agents at which 50% of the erythrocytes in the culture are lysed. Significant hemolysis, as evaluated by HC$_{50}$, was detectable only for peptide gramicidin S (40 µg/mL). In contrast, peptoid oligomers were found to be non-hemolytic. In order to test hemolytic activity of peptoid oligomers further, more stringent parameters were used. Instead of HC$_{50}$, hemolytic concentration$_{10}$ (HC$_{10}$) was used to evaluate hemolytic activity of peptoids used in this study. HC$_{10}$ represents the concentration of antimicrobial agents where 10% of erythrocytes are lysed. HC$_{10}$ values were detectable for only four peptoid oligomers. All of these four peptoid sequences contain Ndp residues, suggesting a relationship between hydrophobicity and hemolytic activity.

Selectivity ratio (SR), which is defined as HC$_{10}$/MIC$_{E.coli}$, measures the ratio of hemolytic activity to antimicrobial activity. High SR values indicate that a compound is a potentially potent and safe antimicrobial reagent and may exhibit a favorable therapeutic index. The SR values obtained in this study range from 0.5 to 32.1 for 20 active compounds (9 linear and 11 cyclic) (Table 2).

The most potent antimicrobial compound in this study, (NapNpm)$_5$, also showed the highest selectivity ratio (>32.1). This indicates that (NapNpm)$_5$ may be safe against human erythrocytes at concentrations for which it is effective against bacterial cells.

TABLE 2

Antimicrobial And Hemolytic Activities of Oligomers Tested In This Study.

| | | MIC µg/mL | | | HC (µg/mL) | | Selectivity |
|---|---|---|---|---|---|---|---|
| # | Compounds | *B. sub* | *E. coli* | *S. aureus* | HC$_{50}$ | HC$_{10}$ | Ratio (SR) |
| 1 | Ac(Gramicidin S) | 7.8 | 125 | 125 | >250 | >250 | >2 |
| 2 | Ac(NgbNpm)$_3$ | 62.5 | 250 | 125 | >250 | >250 | >1 |

TABLE 2-continued

Antimicrobial And Hemolytic Activities of Oligomers Tested In This Study.

| # | Compounds | MIC μg/mL B. sub | MIC μg/mL E. coli | MIC μg/mL S. aureus | HC (μg/mL) HC$_{50}$ | HC (μg/mL) HC$_{10}$ | Selectivity Ratio (SR) |
|---|---|---|---|---|---|---|---|
| 3 | Ac(NahNpm)$_3$ | >500 | >500 | >500 | >250 | >250 | NA |
| 4 | Ac(NapNdp)$_3$ | 1 | 15.6 | 15.6 | >250 | >62.5 | >4 |
| 5 | Ac(NapNnm)$_3$ | 2 | 62.5 | 125 | >250 | >250 | >4 |
| 6 | Ac(NapNpm)$_2$Nap$_2$ | >500 | >500 | >500 | >250 | >250 | NA |
| 7 | Ac(NapNpm)$_3$ | 125 | 125 | 250 | >250 | >250 | >2 |
| 8 | Ac(NapNpm)$_4$ | 31.3 | 250 | 250 | >250 | >250 | >1 |
| 9 | Ac(NapNpm)$_5$ | 15.6 | 31.3 | 62.5 | >250 | >250 | >8 |
| 10 | Ac(NpmNap)$_2$Npm$_2$ | 31.3 | >500 | >500 | >250 | >250 | NA |
| 11 | Ac(NipNapNibNpmPro)$_2$ | >500 | >500 | >500 | >250 | >250 | NA |
| 12 | Ac(NdpNibNgbNipPro)$_2$ | 500 | 250 | 500 | >250 | >250 | >1 |
| 13 | Ac(NpmNibNapNipPro)$_2$ | >500 | >500 | >500 | >250 | >250 | NA |
| 14 | Ac(NabNpm)$_3$ | >500 | >500 | >500 | >250 | >250 | NA |
| 15 | Ac(NgbNdp)$_5$ | 62.5 | 31.3 | 62.5 | >250 | >250 | >8 |
| 16 | Ac(NdpNgb)$_2$Ndp$_2$ | >500 | >500 | 62.5 | >250 | 250 | NA |
| 17 | C(Gramicidin S) | 2 | 15.6 | 15.6 | 40 | >15.6 | 1 |
| 18 | C(NgbNpm)$_3$ | 125 | 250 | 250 | >250 | >250 | >1 |
| 19 | C(NahNpm)$_3$ | 500 | 500 | >500 | >250 | >250 | >0.5 |
| 20 | C(NapNdp)$_3$ | 1 | 15.6 | 7.8 | >250 | >31.3 | >2 |
| 21 | C(NapNnm)$_3$ | 0.5 | 31.3 | 31.3 | >250 | >250 | >8 |
| 22 | C(NapNpm)$_2$Nap$_2$ | >500 | >500 | >500 | >250 | >250 | NA |
| 23 | C(NapNpm)$_3$ | 500 | >500 | 500 | >250 | >250 | NA |
| 24 | C(NapNpm)$_4$ | 2 | 31.3 | 31.3 | >250 | >250 | >8 |
| 25 | C(NapNpm)$_5$ | 0.5 | 7.8 | 7.8 | >250 | >250 | >32.1 |
| 26 | C(NpmNap)$_2$Npm$_2$ | 15.6 | 500 | 500 | >250 | >250 | >0.5 |
| 27 | C(NipNapNibNpmPro)$_2$ | >500 | >500 | >500 | >250 | >250 | NA |
| 28 | C(NdpNibNgbNipPro)$_2$ | 62.5 | 31.3 | 62.5 | >250 | >250 | >8 |
| 29 | C(NpmNibNapNipPro)$_2$ | >500 | >500 | >500 | >250 | >250 | NA |
| 30 | C(NabNpm)$_3$ | 250 | 250 | 500 | >250 | >250 | >1 |
| 31 | C(NgbNdp)$_5$ | 250 | 250 | 250 | >250 | >62.5 | >1 |
| 32 | C(NdpNgb)$_2$Ndp$_2$ | >500 | >500 | >500 | >250 | >250 | NA |

Highlighted in bold type are peptide sequences.
MIC: Minimum Inhibitory Concentration
HC$_{50}$: Hemolytic Concentration 50 (concentration where 50% hemolysis is observed)
HC$_{10}$: Hemolytic Concentration 10 (concentration where 10% hemolysis is observed)
SR = (HC$_{10}$)/(MIC$_{E.\ coli}$)
NA indicates that the compound did not show antimicrobial activity against *E. coli*.

Additional Cyclic Peptoids Prepared or can be Prepared

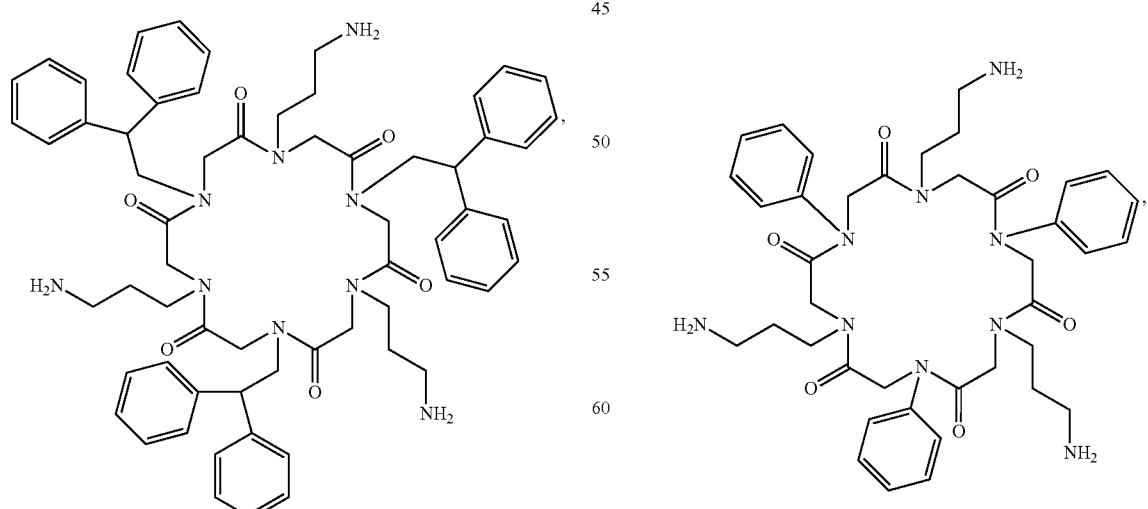

Molecular Weight: 1054.33

Molecular Weight: 741.88

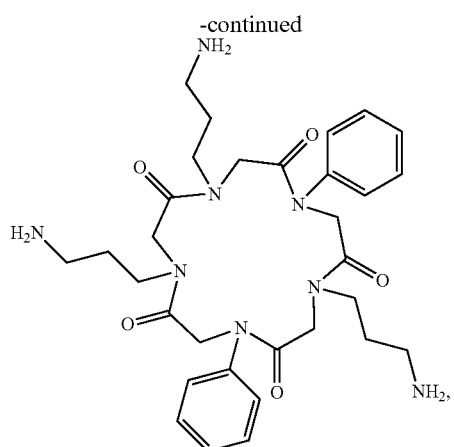
Molecular Weight: 608.73
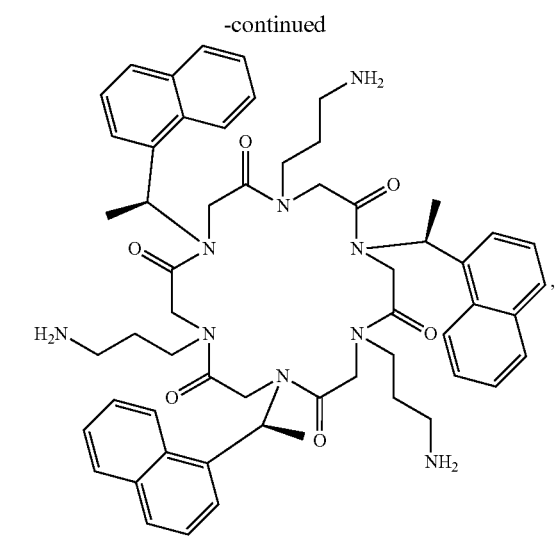
Molecular Weight: 976.21
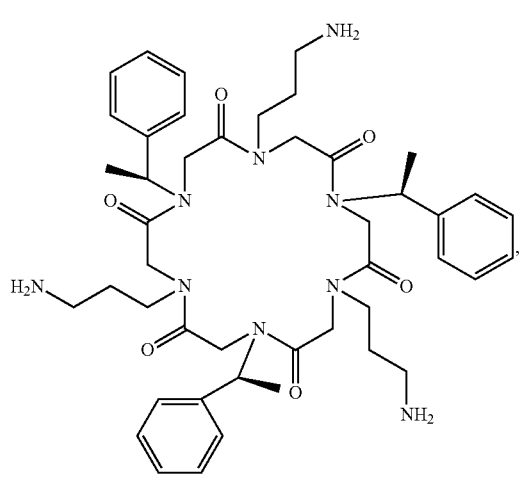
Molecular Weight: 826.04
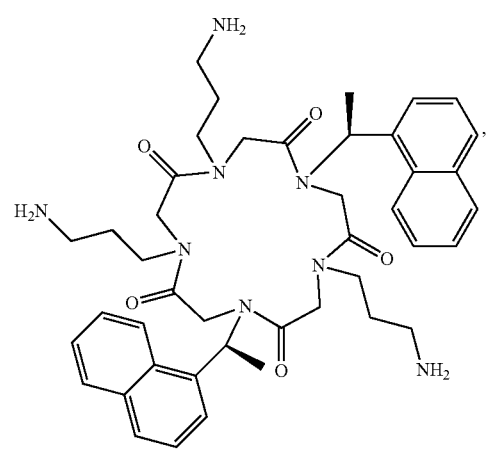
Molecular Weight: 764.96
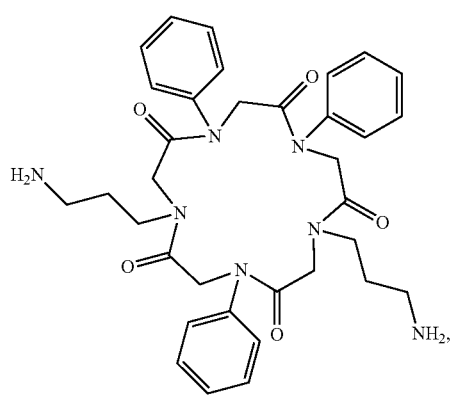
Molecular Weight: 672.73
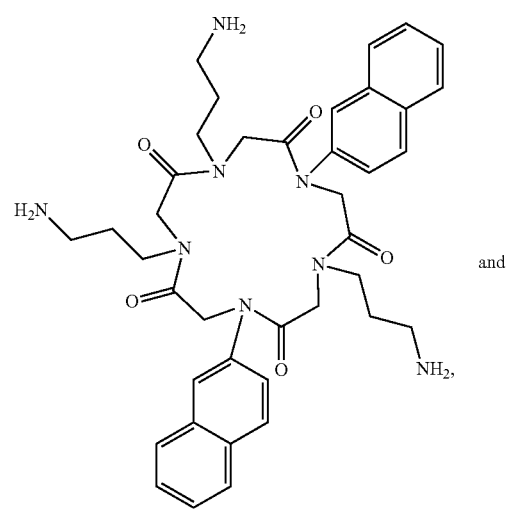
and
Molecular Weight: 708.85

-continued

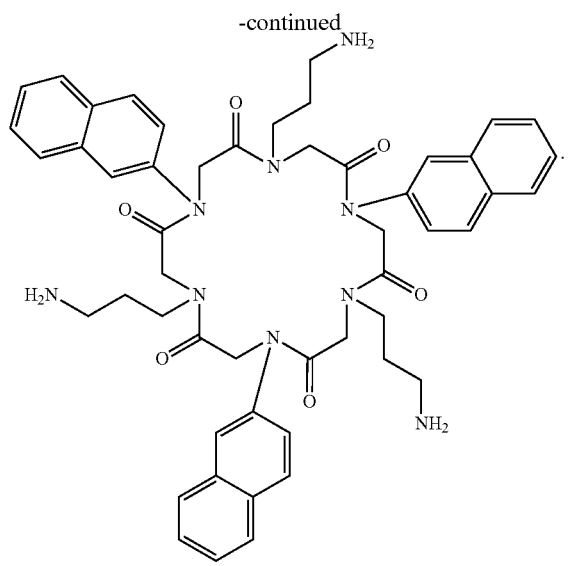

Molecular Weight: 892.05

Effect of Cyclization on Antimicrobial Activity.

After the removal of the Boc protecting groups, all 32 compounds (2 peptide sequences and 30 peptoid sequences) were screened for antimicrobial and hemolytic activity. Antimicrobial activity was tested against the gram-negative strain *Escherichia coli* ATCC 25922, and gram negative strains *Staphylococcus aureus* ATCC 25923, and *Bacillus subtilis* ATCC 6633, according to the guidelines given in the document M07-A7 of the CLSI (Clinical and Laboratory Standards Institute; Clinical and Laboratory Standards Institute. *Methods for Dilution Antimicrobial Susceptibility Tests for Bacteria That Grow Aerobically—Seventh Edition: Approved Standard CLSI document M07-A7. CLSI, Wayne, USA*, 2006). This reference is incorporated herein in its entirety. Hemolytic activity was tested against fresh human erythrocytes.

Out of 16 pairs of N-acetylated linear and cyclic compounds in the library (Table 2), 9 pairs showed enhanced antimicrobial activity through macrocyclization.

Effect of Hydrophobicity on Antimicrobial Activity.

The effect of oligomer hydrophobicity on the antimicrobial activity and hemolytic activity was tested by comparing sequences that incorporate different residues of varying hydrophobicity (Npm, Nnm, and Ndp). Peptoid hexamer sequences were designed to display alternating repeats of cationic and hydrophobic residues. N-acetylated linear and cyclic compounds of (NapNpm)$_3$, (NapNnm)$_3$, and (NapNdp)$_3$ were used to represent three sets of oligomers of varying degrees of hydrophobicity. N-acetylated linear and cyclic (NapNpm)$_3$ oligomers contain three phenyl groups per molecule as the hydrophobic functional groups. These compounds are the least hydrophobic compounds in the group. N-acetylated linear and cyclic (NapNnm)$_3$ oligomers contain three naphthyl groups per molecule as the hydrophobic functional groups. These compounds are expected to be more hydrophobic than (NapNpm)$_3$ oligomers. N-acetylated linear and cyclic (NapNdp)$_3$ oligomers contain six phenyl groups per molecule. These compounds are the most hydrophobic compounds in the group.

Figure 3:
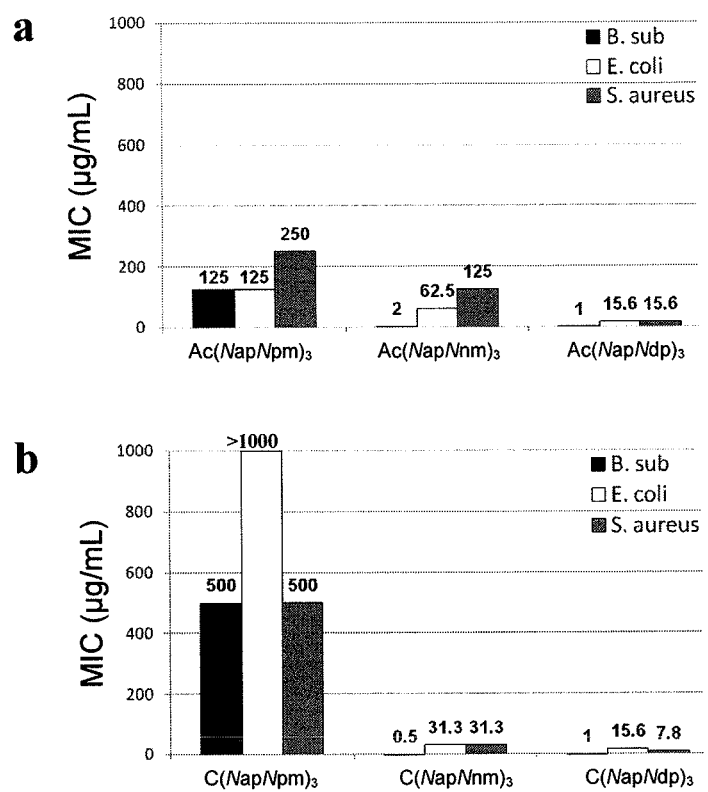
FIG. 3 shows antimicrobial activity data of (a) three linear peptoid oligomers containing different hydrophobic residues and (b) their cyclic counterparts.

Antimicrobial data shown in FIG. 3 demonstrate that the sequences containing Ndp residues show more potent antimicrobial activity than the sequences containing Npm or Nnm residues, suggesting strong co-relationship between hydrophobicity and antimicrobial activity.

Effect of Different Cationic Side Chains on Antimicrobial Activity.

The effect of cationic side chains on the antimicrobial activity was tested by comparing sequences that incorporate different cationic residues (Nap, Nab, Nah, and Ngb). Peptoid hexamer sequences were designed to display alternating repeats of cationic and hydrophobic residues. N-acetylated linear and cyclic compounds of (NapNpm)$_3$, (NabNnm)$_3$, (NahNnm)$_3$, and (NgbNdp)$_3$ were used to represent a set of peptoid oligomers, which were used to study the effect of two different types of cationic functional groups and three different alkyl linker lengths on the antimicrobial activity.

Figure 4:
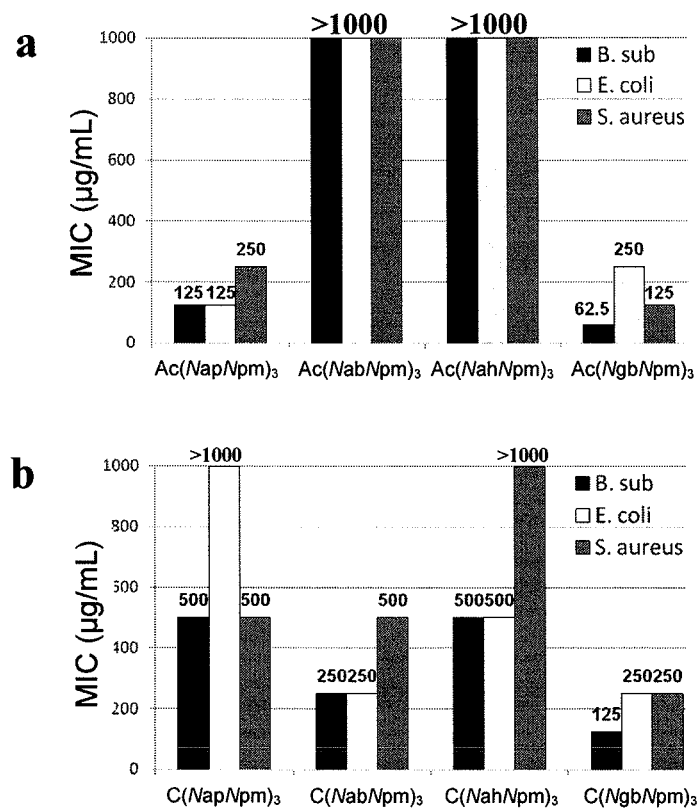
FIG. 4 shows antimicrobial activity data of (a) four linear peptoid oligomers containing different cationic residues and (b) their cyclic counterparts.

Results shown in FIG. 4 indicate that the variations in the length of the amino alkyl side chain or the cationic functional group (amino vs. guanidino) do not markedly alter antimicrobial activity.

Effect of Molecular Size on Antimicrobial Activity.

The effect of molecular size on the antimicrobial activity was tested by comparing hexameric, octameric, and decameric sequences. N-acetylated linear and cyclic compounds of (NapNpm)$_3$, (NapNpm)$_4$, and (NapNpm)$_5$ were used to represent three sets of oligomers of different lengths.

Figure 5:
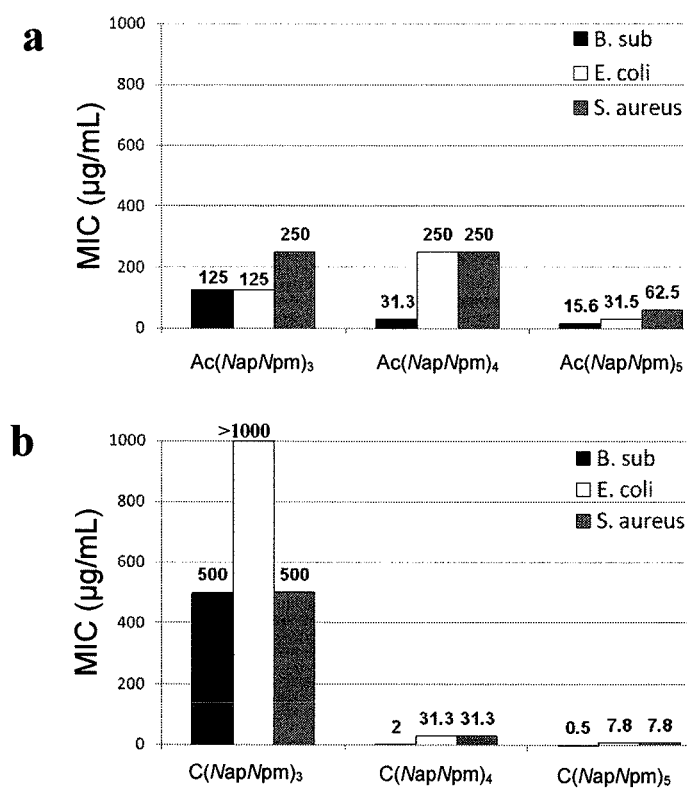
FIG. 5 shows antimicrobial activity data of (a) three linear peptoid oligomers of varying chain lengths and (b) their cyclic counterparts.

FIG. 5 shows that there is a correlation between oligomer length and antimicrobial activity for both linear and cyclic oligomers. For (NapNpm)$_4$, and (NapNpm)$_5$, cyclic compounds are about 8 times more active against bacteria than their N-acetylated linear counterparts. Cyclic (NapNpm)$_4$ has MIC values of 2.0 µg/mL, 31.3 µg/mL, and 31.3 µg/mL for *B. subtilis, E. coli*, and *S. aureus* respectively. Cyclic (NapNpm)$_5$ has MIC values of 0.5 µg/mL, 7.8 µg/mL, and 7.8 µg/mL for *B. subtilis, E. coli*, and *S. aureus* respectively. These two compounds are very active toward both gram positive and gram negative bacterial strains. Interestingly, both of these compounds are non-hemolytic up to 250 µg/mL, providing SR (selective ratio) values of >8.0 and >32.1 for cyclic (NapNpm)$_4$ and cyclic (NapNpm)$_5$ respectively. Such properties make these compounds attractive candidates for therapeutic applications.

Gramicidin S and Gramicidin S Mimetic.

In an effort to capture potent antimicrobial activity found in nature and improve upon its therapeutic application, the inventors have selected gramicidin S as a model compound and generated peptoid gramicidin S mimetics. Gramicidin S is a cyclic decapeptide secreted from *B. brevis*, which shows potent antimicrobial activity against both gram-positive and gram-negative bacteria (Gause et al. *Nature* 1944, 154, 703; Liguori et al. *Nature* 1968, 217, 635-637). Due to its lytic activity against human cells, however, gramicidin S has limited therapeutic applications (Prenner et al. *Biochim. BioPhys. Acta* 1999, 1462, 201-221; Lee et al. *J. Peptide Res.* 2004, 63, 69-84). Two peptide sequences (N-acetylated linear and cyclic forms of gramicidn S) and six peptoid sequences (N-acetylated linear and cyclic forms of (Nip-NapNibNpmPro)$_2$, (NpmNibNapNipPro)$_2$ and (NdpNibNgbNipPro)$_2$) were generated. The peptoid sequences display the side chain chemical functionalities found in gramicidin S.

Figure 6:
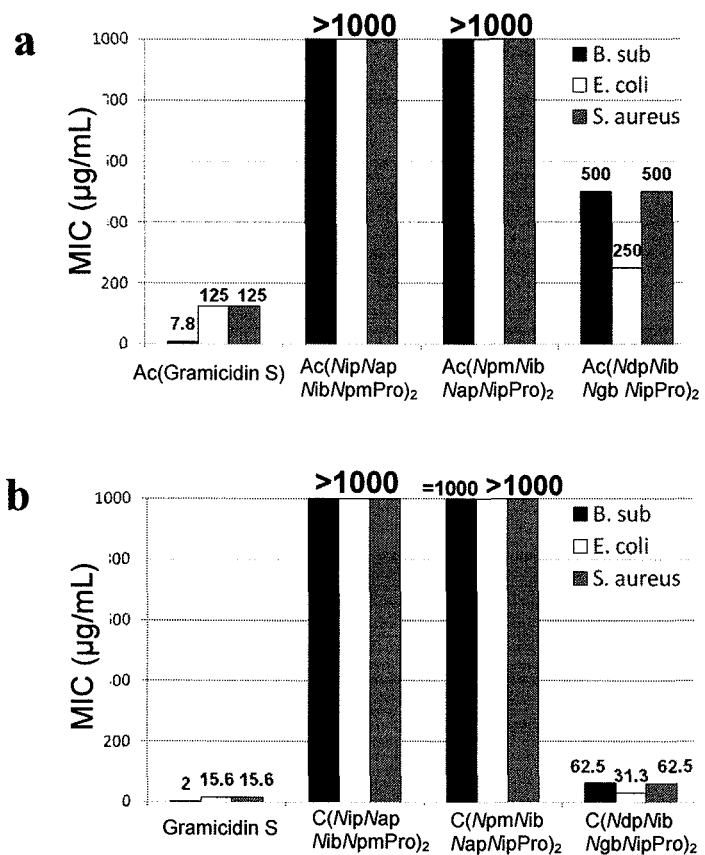
FIG. 6 shows antimicrobial activity data of (a) an N-acetylated linear peptide gramicidin S sequence and three peptoid sequences and (b) their cyclic counterparts. The MIC value of C(NpmNibNapNipPro)$_2$ for *B. subtilis* was 1000 µg/mL, for *E. coli* and *S. aureus* were greater than 1000 µg/mL.

The results shown in FIG. 6 indicate that gramicidin has antimicrobial activity. MIC values of gramicidin S are 2.0 µg/mL for *B. subtilis,* 15.6 µg/mL for *E. coli,* and 15.6 µg/mL for *S. aureus*.

Example 2

Antibacterial Testing Against *S. aureus* Strains

Experimental Design:

Twelve strains of MSSA (methicillin-sensitive) and MRSA (methicillin-resistant) *S. aureus* were cross-tested against two antibacterial peptoid oligomers.

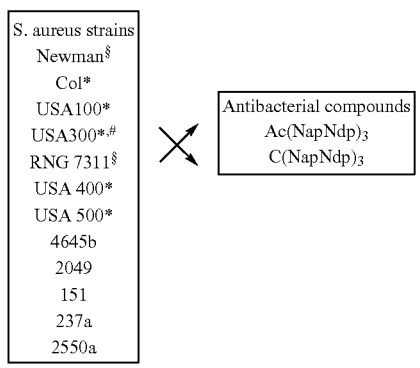

* MRSA strains, all other strains are MSSA.
§ Clinical isolates
Major epidemic strain of MRSA Testing was accomplished with 96-well plates wherein each well contained LB media, the *S. aureus* strain, and a solution of the compound in ethanol at a specific concentration.

A twofold serial dilution of each compound was accomplished with pure ethanol starting from 0.5 mg/mL to 0.0039 mg/mL.

To determine the appropriate concentration of the bacterial strain for each well, the previously grown (overnight in LB media) cultures were diluted with LB media until the optical density at 595 nm ($OD_{595} \sim OD_{600}$) was ~0.005.

Each experiment was conducted in triplicate, e.g. testing of "Newman" *S. aureus* strain against a specific concentration of C(NapNdp)$_3$ was replicated in three wells.

Control experiments were also conducted in absence of the compound, i.e. the plates contained only the bacterial strain, LB media, and ethanol.

The plates were incubated and gently shaken overnight (20 hours) at 37° C., and $OD_{595}$ was read before (t=0) and after (t=20) incubation.

Analysis:

$OD_{595}$ at t=0 for each well was averaged over the three trials, and this value was subtracted from $OD_{595}$ at t=20 hr for each well.

The minimum inhibitory concentration (MIC) was taken as the lowest concentration which exhibited growth inhibition. Specifically, along a dilution sequence, the well with the least $OD_{595}$ after subtraction was determined to be the MIC.

Results and Summary:

TABLE 3

Antimicrobial properties of Ac(NapNdp)$_3$ and C(NapNdp)$_3$ on *S. aureus* strains
MIC (µg/mL) of compounds against *Staphylococcus aureus* strains

|  | Ac(NapNdp)$_3$ | C(NapNdp)$_3$ |
| --- | --- | --- |
| Newman | 15.6 | 3.91 |
| Col | 15.6 | 3.91 |
| USA100 | 15.6 | 3.91 |
| USA300 | 15.6 | 3.91 |
| RNG7311 | 15.6 | 3.91 |
| USA400 | 15.6 | 3.91 |
| USA500 | 15.6 | 3.91 |
| 4645b | 15.6 | 7.81 |
| 2049 | 15.6 | 7.81 |
| 151 | 15.6 | 3.91 |
| 237a | 15.6 | 3.91 |
| 2550a | 15.6 | 3.91 |

The results indicate good correlation with previous experiments, and show that both compounds Ac(NapNdp)$_3$ and C(NapNdp)$_3$ are active across clinical, community-acquired, and hospital strains of *Staphylococcus aureus*. Activity against methicillin-sensitive and methicillin-resistant strains of *S. aureus* is also shown. The difference in MICs between the two compounds also indicates that an increase in conformational order (macrocylization of sequences) increases the potency.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for peptoid oligomers are approximate, and are provided for description.

All publications, including but not limited to patents and patent applications, cited in this specification are herein incorporated by reference as if each individual publication were specifically and individually indicated to be incorporated by reference herein as though fully set forth.

What is claimed is:

1. A method for treating, ameliorating or managing a disease or condition, which comprises administering to a patient in need of such treatment, amelioration or management a therapeutically acceptable amount of a peptoid oligomer according to formula Ib

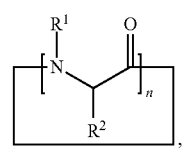

Ib a salt, stereoisomers, isotopic variants, or tautomers thereof;

wherein each R$^1$ is independently substituted or unsubstituted alkyl; each R$^2$ is independently hydrogen, or substituted or unsubstituted alkyl; or each R$^1$ and R$^2$ are joined together to form a 4-7 membered heterocyclic ring; the said peptoid oligomer consists of one or more monomers selected from Nap, Nab, Nah, Ngb, Npm, Nnm, Ndp, Nip, Nib and Pro:

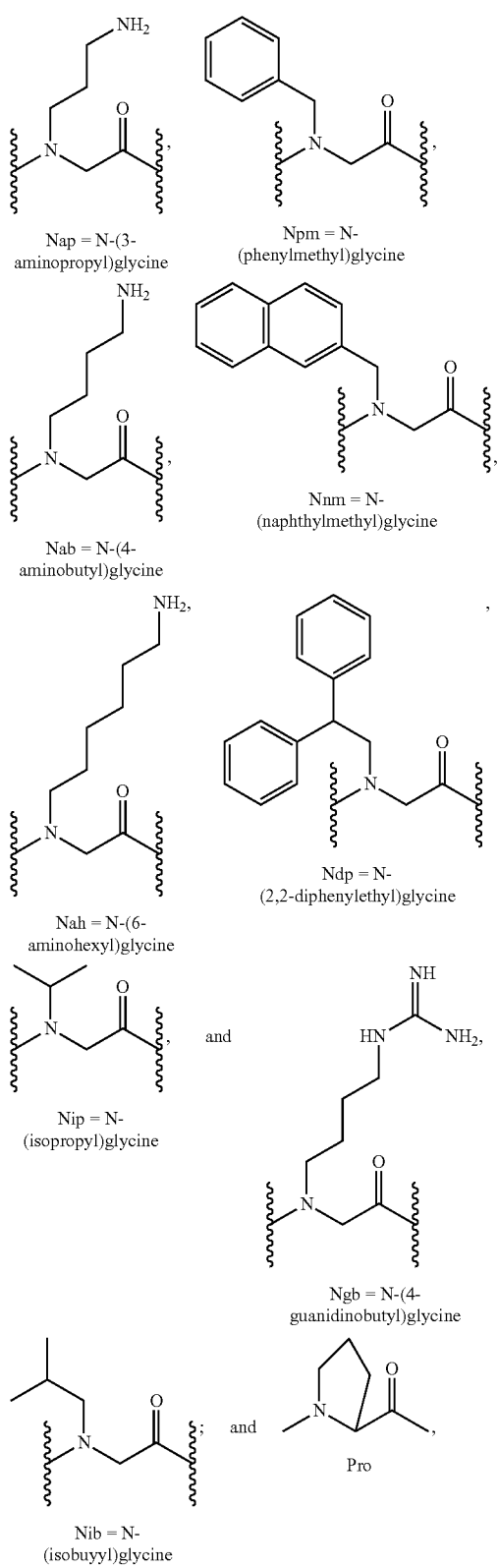

and n is an integer between 4 and 20; and at least one of the monomers in the peptoid oligomer is Nap, Nab, Nah, or Ngb.

2. A peptoid oligomer according to formula Ib

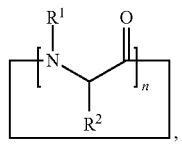

a salt, stereoisomers, isotopic variants, or tautomers thereof;

wherein each $R^1$ is independently substituted or unsubstituted alkyl;

each $R^2$ is independently hydrogen, or substituted or unsubstituted alkyl; or each $R^1$ and $R^2$ are joined together to form a 4-7 membered heterocyclic ring;

the said peptoid oligomer consists of one or more monomers selected from Nap, Nab, Nah, Ngb, Npm, Nnm, Ndp, Nip, Nib and Pro:

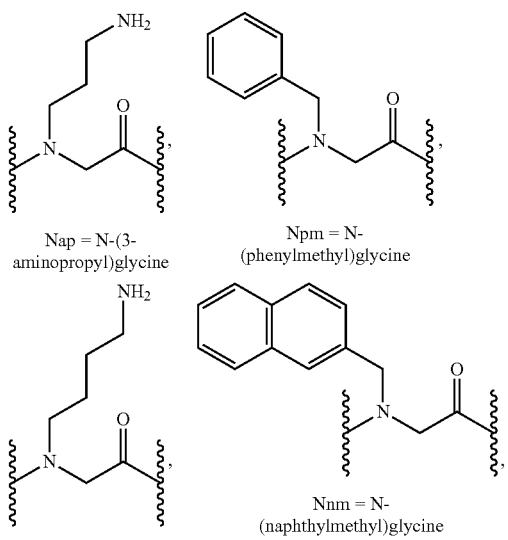

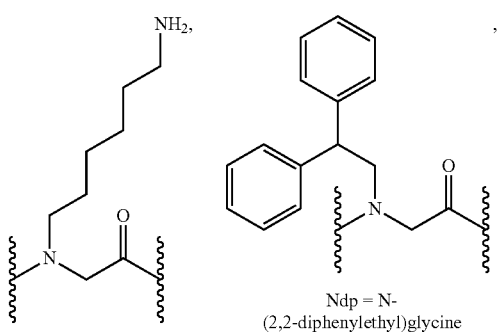

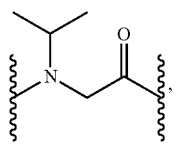

Nip = N-(isopropyl)glycine

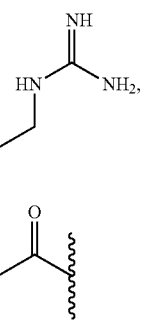

Ngb = N-(4-guanidinobutyl)glycine

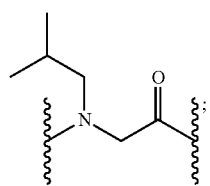

Nib = N-(isobuyyl)glycine

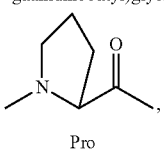

Pro n is an integer between 4 and 20; and at least one of the monomers in the peptoid oligomer is Nap, Nab, Nah, or Ngb.

3. The method of claim 1, wherein the disease or condition is or results from a bacterial infection.

4. The method of claim 1, wherein the disease or condition is or results from a viral infection.

5. The method of claim 1, wherein the disease or condition is or results from a fungal infection.

6. The method of claim 1, wherein the disease or condition is or results from gram positive or gram negative bacterial strain infection.

7. The method of claim 1, wherein the disease or condition is or results from abnormal behaviors of essential proteins.

8. The method of claim 1, wherein the disease or condition is or results from *Staphylococcus aureus, Streptococcus pneumoniae*, or *Pseudomonas aeruginosa* infection.

9. The method of claim 1, wherein the disease or condition is or results from Methicillin-resistant *Staphylococcus aureus* (MRSA) infection.

10. A method for generating an antiseptic or sterile environment, which comprises applying at least one peptoid oligomer according to claim 1 or a composition thereof to a surface of the environment to coat the surface, thereby generating the antiseptic or sterile environment.

11. An antimicrobial or pharmaceutical composition comprising at least one peptoid oligomer according to claim 2.

12. An antimicrobial substrate comprising at least one peptoid oligomer according to claim 2 bound to or incorporated into the substrate.

13. An article comprising an antimicrobial substrate of claim 12, wherein the article is selected from the group consisting of a personal care item, an agricultural item, a cosmetic, a package, a food handling item, a food delivery item, a personal garment, a medical device, a personal hygiene item, an article intended for oral contact, a household item, a toy, and a liquid separation article.

14. A method for treating, ameliorating or managing a disease or condition, which comprises administering to a patient in need of such treatment, amelioration or management a therapeutically acceptable amount of at least one peptoid oligomer according to claim 2 or a composition thereof to the patient.

15. A method for generating an antiseptic or sterile environment, which comprises applying at least one peptoid oligomer according to claim 2 or a composition thereof to a surface of the environment to coat the surface, thereby generating the antiseptic or sterile environment.

16. The peptoid oligomer according to claim 2, wherein n is 6; and the said peptoid oligomer consists of three Ngb, Nah, Nap or Nab monomers; and three Ndp, Nnm, or Npm, monomers.

17. The peptoid oligomer according to claim 2, wherein n is 6; and the said peptoid oligomer consists of four Nap monomers; and two Npm monomers.

18. The peptoid oligomer according to claim 2, wherein n is 6; and the said peptoid oligomer consists of four Npm monomers; and two Nap monomers.

19. The peptoid oligomer according to claim 2, wherein n is 6; and the said peptoid oligomer consists of four Ndp monomers; and two Ngb monomers.

20. The peptoid oligomer according to claim 2, wherein n is 8; and the said peptoid oligomer consists of four Nap monomers; and four Npm monomers.

21. The peptoid oligomer according to claim 2, wherein n is 10; and the said peptoid oligomer consists of two Nip monomers; two Nap monomers; two Nib monomers; two Npm monomers; and two Pro monomers.

22. The peptoid oligomer according to claim 2, wherein n is 10; and the said peptoid oligomer consists of two Ndp monomers; two Nib monomers; two Ngb monomers; two Nip monomers; and two Pro monomers.

23. The peptoid oligomer according to claim 2, wherein n is 10; and the said peptoid oligomer consists of two Npm monomers; two Nib monomers; two Nap monomers; two Nip monomers; and two Pro monomers.

24. The peptoid oligomer according to claim 2, wherein n is 10; and the said peptoid oligomer consists of five Nap monomers; and five Npm monomers.

25. The peptoid oligomer according to claim 2, wherein n is 10; and the said peptoid oligomer consists of five Ngb monomers; and five Ndp monomers.

26. The peptoid oligomer according to claim 2, selected from the group consisting of:
C(NgbNpm)$_3$;
C(NahNpm)$_3$;
C(NapNdp)$_3$;
C(NapNnm)$_3$;
C(NapNpm)$_2$Nap$_2$;
C(NapNpm)$_3$;
C(NapNpm)$_4$;
C(NapNpm)$_5$;
C(NpmNap)$_2$Npm$_2$;
C(NipNapNibNpmPro)$_2$;
C(NdpNibNgbNipPro)$_2$;
C(NpmNibNapNipPro)$_2$;
C(NabNpm)$_3$;
C(NgbNdp)$_5$; and
C(NdpNgb)$_2$Ndp$_2$
wherein C is cyclic.

27. The peptoid oligomer according to claim 2, selected from the group consisting of:
C(NapNdp)$_3$;
C(NapNpm)$_3$; and
C(NapNpm)$_5$;
wherein C is cyclic.

28. A pharmaceutical composition comprising a pharmaceutically acceptable carrier and a pharmaceutically effective amount of the peptoid oligomer of claim 2.

29. The pharmaceutical composition of claim 28, wherein the carrier is a parenteral carrier, oral or topical carrier.

* * * * *